United States Patent
Mikhaylik et al.

(10) Patent No.: US 11,569,531 B2
(45) Date of Patent: Jan. 31, 2023

(54) ADDITIVES FOR ELECTROCHEMICAL CELLS

(71) Applicant: Sion Power Corporation, Tucson, AZ (US)

(72) Inventors: Yuriy V. Mikhaylik, Tucson, AZ (US); Igor P. Kovalev, Vail, AZ (US); Thomas Weiss, Ilvesheim (DE)

(73) Assignee: Sion Power Corporation, Tucson, AZ (US)

( * ) Notice: Subject to any disclaimer, the term of this patent is extended or adjusted under 35 U.S.C. 154(b) by 27 days.

(21) Appl. No.: 17/366,539

(22) Filed: Jul. 2, 2021

(65) Prior Publication Data

US 2021/0408598 A1  Dec. 30, 2021

Related U.S. Application Data

(63) Continuation of application No. 16/742,340, filed on Jan. 14, 2020, now Pat. No. 11,088,395, which is a
(Continued)

(51) Int. Cl.
*H01M 10/0567* (2010.01)
*C07D 295/194* (2006.01)
(Continued)

(52) U.S. Cl.
CPC ....... *H01M 10/0567* (2013.01); *C07C 327/36* (2013.01); *C07D 295/194* (2013.01);
(Continued)

(58) Field of Classification Search
CPC ........................ H01M 10/052; H01M 10/0567
See application file for complete search history.

(56) References Cited

U.S. PATENT DOCUMENTS 5,154,990 A 10/1992 Plichta et al.
5,648,187 A 7/1997 Skotheim
(Continued)

FOREIGN PATENT DOCUMENTS

CN 103427068 A 12/2013
CN 104269575 A 1/2015
(Continued)

OTHER PUBLICATIONS

Extended European Search Report for EP 16198477.8 dated Feb. 16, 2017.
(Continued)

*Primary Examiner* — Amanda C. Walke
(74) *Attorney, Agent, or Firm* — Wolf, Greenfield & Sacks, P.C.

(57) ABSTRACT

Articles and methods including additives in electrochemical cells, are generally provided. As described herein, such electrochemical cells may comprise an anode, a cathode, an electrolyte, and optionally a separator. In some embodiments, at least one of the anode, the cathode, the electrolyte, and/or the optional separator may comprise an additive and/or additive precursor. For instance, in some cases, the electrochemical cell comprises an electrolyte and an additive and/or additive precursor that is soluble with and/or is present in the electrolyte. In some embodiments, the additive precursor comprises a disulfide bond. In certain embodiments, the additive is a carbon disulfide salt. In some cases, the electrolyte may comprise a nitrate.

20 Claims, 10 Drawing Sheets

Related U.S. Application Data continuation of application No. 16/299,247, filed on Mar. 12, 2019, now Pat. No. 10,541,448, which is a continuation of application No. 15/349,140, filed on Nov. 11, 2016, now Pat. No. 10,320,031.

(60) Provisional application No. 62/254,818, filed on Nov. 13, 2015.

(51) Int. Cl.
| | |
|---|---|
| *H01M 4/40* | (2006.01) |
| *C07C 327/36* | (2006.01) |
| *H01M 10/0568* | (2010.01) |
| *H01M 4/38* | (2006.01) |
| *H01M 4/58* | (2010.01) |
| *H01M 4/02* | (2006.01) |
| *H01M 8/12* | (2016.01) |
| *H01M 10/052* | (2010.01) |

(52) U.S. Cl.
CPC ....... *H01M 4/405* (2013.01); *H01M 10/0568* (2013.01); *H01M 4/38* (2013.01); *H01M 4/382* (2013.01); *H01M 4/5815* (2013.01); *H01M 10/052* (2013.01); *H01M 2004/027* (2013.01); *H01M 2004/028* (2013.01); *H01M 2008/1293* (2013.01); *H01M 2300/0025* (2013.01)

(56) References Cited

U.S. PATENT DOCUMENTS

| | | |
|---|---|---|
| 5,695,887 A | 12/1997 | Amatucci et al. |
| 5,756,232 A | 5/1998 | Kelly et al. |
| 5,919,587 A | 7/1999 | Mukherjee et al. |
| 5,961,672 A | 10/1999 | Skotheim et al. |
| 6,053,953 A | 4/2000 | Tomiyama et al. |
| 6,114,068 A | 9/2000 | Yamada et al. |
| 6,159,640 A | 12/2000 | Appel et al. |
| 6,183,901 B1 | 2/2001 | Ying et al. |
| 6,238,821 B1 | 5/2001 | Mukherjee et al. |
| 6,733,924 B1 | 5/2004 | Skotheim et al. |
| 6,797,428 B1 | 9/2004 | Skotheim et al. |
| 6,936,381 B2 | 8/2005 | Skotheim et al. |
| 7,247,408 B2 | 7/2007 | Skotheim et al. |
| 7,544,244 B2 | 6/2009 | Sakashita et al. |
| 7,547,491 B2 | 6/2009 | Ham et al. |
| 7,553,590 B2 | 6/2009 | Mikhaylik |
| 7,688,075 B2 | 3/2010 | Kelley et al. |
| 7,771,870 B2 | 8/2010 | Affinito et al. |
| 7,785,730 B2 | 8/2010 | Affinito et al. |
| 7,829,219 B2 | 11/2010 | Yun et al. |
| 7,939,198 B2 | 5/2011 | Mukherjee et al. |
| 8,076,024 B2 | 12/2011 | Affinito et al. |
| 8,084,102 B2 | 12/2011 | Affinito |
| 8,087,309 B2 | 1/2012 | Kelley et al. |
| 8,105,717 B2 | 1/2012 | Skotheim et al. |
| 8,173,301 B2 | 5/2012 | Hiratsuka et al. |
| 8,197,971 B2 | 6/2012 | Skotheim et al. |
| 8,264,205 B2 | 9/2012 | Kopera |
| 8,337,948 B2 | 12/2012 | Kawaoka |
| 8,338,034 B2 | 12/2012 | Affinito et al. |
| 8,415,054 B2 | 4/2013 | Skotheim et al. |
| 8,603,680 B2 | 12/2013 | Affinito et al. |
| 8,617,748 B2 | 12/2013 | Mikhaylik et al. |
| 8,623,557 B2 | 1/2014 | Skotheim et al. |
| 8,728,661 B2 | 5/2014 | Skotheim et al. |
| 8,753,771 B2 | 6/2014 | Skotheim et al. |
| 8,871,387 B2 | 10/2014 | Wang et al. |
| 8,936,870 B2 | 1/2015 | Affinito et al. |
| 8,968,928 B2 | 3/2015 | Wang et al. |
| 9,005,311 B2 | 4/2015 | Safont et al. |
| 9,005,809 B2 | 4/2015 | Wilkening et al. |
| 9,034,421 B2 | 5/2015 | Mikhaylik et al. |
| 9,040,197 B2 | 5/2015 | Affinito et al. |
| 9,040,201 B2 | 5/2015 | Affinito et al. |
| 9,065,149 B2 | 6/2015 | Skotheim et al. |
| 9,077,041 B2 | 7/2015 | Burnside et al. |
| 9,105,938 B2 | 8/2015 | Scordilis-Kelley et al. |
| 9,196,903 B2 | 11/2015 | Tokuda |
| 9,214,678 B2 | 12/2015 | Mikhaylik |
| 9,337,483 B2 | 5/2016 | Geng |
| 9,397,342 B2 | 7/2016 | Skotheim et al. |
| 9,419,274 B2 | 8/2016 | Wilkening et al. |
| 9,472,808 B2 | 10/2016 | Engel et al. |
| 9,490,478 B2 | 11/2016 | Mikhaylik et al. |
| 9,531,009 B2 | 12/2016 | Kumaresan et al. |
| 9,548,492 B2 | 1/2017 | Affinito et al. |
| 9,559,348 B2 | 1/2017 | Kumaresan et al. |
| 9,577,243 B2 | 2/2017 | Schmidt et al. |
| 9,577,267 B2 | 2/2017 | Scordilis-Kelley et al. |
| 9,653,735 B2 | 5/2017 | Skotheim et al. |
| 9,653,750 B2 | 5/2017 | Laramie et al. |
| 9,711,784 B2 | 7/2017 | Kelley et al. |
| 9,728,768 B2 | 8/2017 | Mikhaylik et al. |
| 9,735,411 B2 | 8/2017 | Viner et al. |
| 9,748,605 B2 | 8/2017 | Schmidt et al. |
| 9,755,268 B2 | 9/2017 | Fleischmann et al. |
| 9,780,404 B2 | 10/2017 | Scordilis-Kelley et al. |
| 9,825,328 B2 | 11/2017 | Du et al. |
| 9,853,287 B2 | 12/2017 | Mikhaylik et al. |
| 9,947,963 B2 | 4/2018 | Du et al. |
| 9,994,959 B2 | 6/2018 | Laramie et al. |
| 9,994,960 B2 | 6/2018 | Laramie et al. |
| 10,020,479 B2 | 7/2018 | Mikhaylik et al. |
| 10,020,512 B2 | 7/2018 | Gronwald et al. |
| 10,050,308 B2 | 8/2018 | Liao et al. |
| 10,069,135 B2 | 9/2018 | Fleischmann et al. |
| 10,069,146 B2 | 9/2018 | Skotheim et al. |
| 10,079,405 B2 | 9/2018 | Smith et al. |
| 10,320,031 B2 | 6/2019 | Mikhaylik et al. |
| 10,541,448 B2 | 1/2020 | Mikhaylik et al. |
| 10,868,306 B2 | 12/2020 | Mudalige et al. |
| 10,944,094 B2 | 3/2021 | Liao et al. |
| 11,088,395 B2 | 8/2021 | Mikhaylik et al. |
| 2003/0190530 A1 | 10/2003 | Yang et al. |
| 2004/0076887 A1 | 4/2004 | Panitz et al. |
| 2005/0019670 A1 | 1/2005 | Amine et al. |
| 2005/0053841 A1 | 3/2005 | Ivanov et al. |
| 2005/0196672 A1 | 9/2005 | Mukherjee et al. |
| 2006/0115579 A1 | 6/2006 | Mukherjee et al. |
| 2007/0221265 A1 | 9/2007 | Affinito et al. |
| 2007/0292756 A1 | 12/2007 | Tsuchiya |
| 2008/0318128 A1 | 12/2008 | Simoneau et al. |
| 2009/0035646 A1 | 2/2009 | Mikhaylik et al. |
| 2009/0055110 A1 | 2/2009 | Kelley et al. |
| 2009/0286157 A1 | 11/2009 | Chen et al. |
| 2010/0239914 A1 | 9/2010 | Mikhaylik et al. |
| 2011/0006738 A1 | 1/2011 | Mikhaylik et al. |
| 2011/0014524 A1 | 1/2011 | Skotheim et al. |
| 2011/0068001 A1 | 3/2011 | Affinito et al. |
| 2011/0070491 A1 | 3/2011 | Campbell et al. |
| 2011/0070494 A1 | 3/2011 | Campbell et al. |
| 2011/0076560 A1 | 3/2011 | Scordilis-Kelley et al. |
| 2011/0159376 A1 | 6/2011 | Skotheim et al. |
| 2011/0165471 A9 | 7/2011 | Skotheim et al. |
| 2011/0177398 A1 | 7/2011 | Affinito et al. |
| 2011/0206992 A1 | 8/2011 | Campbell et al. |
| 2011/0256450 A1 | 10/2011 | Campbell et al. |
| 2012/0048729 A1 | 3/2012 | Mikhaylik et al. |
| 2012/0052339 A1 | 3/2012 | Mikhaylik et al. |
| 2012/0052397 A1 | 3/2012 | Mikhaylik et al. |
| 2012/0070746 A1 | 3/2012 | Mikhaylik et al. |
| 2012/0082872 A1 | 4/2012 | Schmidt et al. |
| 2012/0082901 A1 | 4/2012 | Schmidt et al. |
| 2012/0171578 A1 | 7/2012 | Zhang et al. |
| 2013/0164635 A1 | 6/2013 | Schmidt et al. |
| 2013/0196206 A1 | 8/2013 | Park et al. |
| 2013/0316072 A1 | 11/2013 | Scordilis-Kelley et al. |
| 2014/0002942 A1 | 1/2014 | Song et al. |
| 2014/0062411 A1 | 3/2014 | Mikhaylik et al. |
| 2014/0079994 A1 | 3/2014 | Affinito et al. |
| 2014/0127419 A1 | 5/2014 | Fleischmann et al. |
| 2014/0127577 A1 | 5/2014 | Fleischmann et al. |

(56) References Cited

U.S. PATENT DOCUMENTS

| | | |
|---|---|---|
| 2014/0199591 A1 | 7/2014 | Geng |
| 2014/0272565 A1 | 9/2014 | Gronwald et al. |
| 2014/0272594 A1 | 9/2014 | Safont et al. |
| 2014/0272595 A1 | 9/2014 | Cristadoro et al. |
| 2014/0272597 A1 | 9/2014 | Mikhaylik et al. |
| 2014/0377668 A1 | 12/2014 | Abe et al. |
| 2015/0010804 A1 | 1/2015 | Laramie et al. |
| 2015/0044517 A1 | 2/2015 | Mikhaylik et al. |
| 2015/0079466 A1 | 3/2015 | Yoon |
| 2015/0086837 A1 | 3/2015 | Laramie et al. |
| 2015/0162586 A1 | 6/2015 | Fleischmann et al. |
| 2015/0171469 A1 | 6/2015 | Kourtakis et al. |
| 2015/0180037 A1 | 6/2015 | Gronwald et al. |
| 2015/0180084 A1 | 6/2015 | Scordilis-Kelley et al. |
| 2015/0188194 A1 | 7/2015 | Mikhaylik et al. |
| 2015/0200422 A1 | 7/2015 | Lee et al. |
| 2015/0236320 A1 | 8/2015 | Laramie et al. |
| 2015/0236322 A1 | 8/2015 | Laramie et al. |
| 2015/0280277 A1 | 10/2015 | Fleischmann et al. |
| 2015/0287986 A1 | 10/2015 | Affinito et al. |
| 2015/0287998 A1 | 10/2015 | Scordilis-Kelley et al. |
| 2015/0288033 A1 | 10/2015 | Lee et al. |
| 2015/0290834 A1 | 10/2015 | Klotz et al. |
| 2015/0318539 A1 | 11/2015 | Kelley et al. |
| 2015/0340736 A1 | 11/2015 | Kim et al. |
| 2015/0349310 A1 | 12/2015 | Viner et al. |
| 2015/0372349 A1 | 12/2015 | Shikita |
| 2016/0072132 A1 | 3/2016 | Liao et al. |
| 2016/0118638 A1 | 4/2016 | Gronwald et al. |
| 2016/0118651 A1 | 4/2016 | Kovalev et al. |
| 2016/0248121 A1 | 8/2016 | Uematsu et al. |
| 2016/0301080 A1 | 10/2016 | Skotheim et al. |
| 2016/0344067 A1 | 11/2016 | Laramie et al. |
| 2016/0372789 A1 | 12/2016 | Cheng et al. |
| 2017/0018815 A1 | 1/2017 | Laramie et al. |
| 2017/0047590 A1 | 2/2017 | Mikhaylik et al. |
| 2017/0141385 A1 | 5/2017 | Scordilis-Kelley et al. |
| 2017/0141402 A1 | 5/2017 | Affinito et al. |
| 2017/0141442 A1 | 5/2017 | Mikhaylik et al. |
| 2017/0149086 A1 | 5/2017 | Du et al. |
| 2017/0200975 A1 | 7/2017 | Liao et al. |
| 2017/0250390 A1 | 8/2017 | Laramie et al. |
| 2017/0288208 A1 | 10/2017 | Kelley et al. |
| 2017/0338475 A1 | 11/2017 | Laramie et al. |
| 2017/0352863 A1 | 12/2017 | Mikhaylik et al. |
| 2017/0373321 A1 | 12/2017 | Skotheim et al. |
| 2018/0006303 A1 | 1/2018 | Mikhaylik et al. |
| 2018/0034100 A1 | 2/2018 | Du et al. |
| 2018/0048018 A1 | 2/2018 | Scordilis-Kelley et al. |
| 2018/0138542 A1 | 5/2018 | Bunte et al. |
| 2018/0198162 A1 | 7/2018 | Du et al. |
| 2018/0230610 A1 | 8/2018 | Laramie et al. |
| 2018/0254516 A1 | 9/2018 | Han et al. |
| 2018/0261820 A1 | 9/2018 | Liao et al. |
| 2018/0269520 A1 | 9/2018 | Scordilis-Kelley et al. |
| 2018/0277850 A1 | 9/2018 | Quero-Mieres et al. |
| 2018/0287122 A1 | 10/2018 | Mikhaylik et al. |
| 2018/0337406 A1 | 11/2018 | Mudalige et al. |
| 2018/0351158 A1 | 12/2018 | Liao et al. |
| 2019/0267669 A1 | 8/2019 | Mikhaylik et al. |
| 2020/0227785 A1 | 7/2020 | Mikhaylik et al. |
| 2021/0265610 A1 | 8/2021 | Liao et al. |

FOREIGN PATENT DOCUMENTS

| | | |
|---|---|---|
| EP | 0 539 256 | 4/1993 |
| EP | 2 144 321 | 1/2010 |
| EP | 3 002 814 | 4/2016 |
| JP | S52-023623 A | 2/1977 |
| JP | H06-36797 A | 2/1994 |
| JP | 2001-253904 A | 9/2001 |
| JP | 2004-055471 A | 2/2004 |
| JP | 2005-310482 A | 11/2005 |
| JP | 2006-179325 A | 7/2006 |
| JP | 2007-128723 A | 5/2007 |

OTHER PUBLICATIONS

International Search Report and Written Opinion for PCT/US2016/061538 dated Feb. 24, 2017.

[No Author Listed], 2,2,2-Trifluoroethyl dimethylcarbamate. Alfa Chemistry. 5 pages. [last accessed Jul. 15, 2020].

[No Author Listed], Carbamate. PubChem. 17 pages. [last accessed Jul. 20, 2020].

[No Author Listed], NIST Standard Reference Database 101. CCCBDB. 30 pages. [last accessed Jul. 20, 2020].

[No Author Listed], Propylene carbonate. PubChem. 51 pages. [last accessed Jul. 20, 2020].

Barany et al., A general strategy for elaboration of the dithiocarbonyl functionality,–(C:O)SS–: application to the synthesis of bis(chlorocarbonyl)disulfane and related derivatives of thiocarbonic acids. J. Org. Chem. Dec. 1983;48:4750-61.

Doeff, Battery Cathodes. Batteries for Sustainability: Selected Entries from the Encyclopedia of Sustainability Science and Technology—Chapter 2. R.J. Brodd (ed.). Springer. New York. 2013:5-49.

Etacheri et al., Challenges in the development of advanced Li-ion batteries: a review. Energy & Environmental Science. Aug. 2011:20 pages.

Hu et al., Effect of lithium difluoro(oxalate)borate (LiDFOB) additive on the performance of high-voltage lithium-ion batteries. J. Appl. Electrochem. 2012;42:291-6. Epub Mar. 23, 2012.

Liu et al., Electrode Kinetics of Organodisulfide Cathodes for Storage Batteries. Mar. 1990;137(3):750-9.

Liu et al., Functional lithium borate salts and their potential application in high performance lithium batteries. Coordination Chemistry Reviews. 2015;292:56-73. Epub Feb. 19, 2015.

Vigdergauz et al., The wettability of electrodes made of natural metal sulfides. Journal of Solid State Electrochemistry. Jan. 1998;2(1):50-7.

Visco et al., Ambient Temperature High-Rate Lithium/Organosulfur Batteries. J. Electrochem. Soc. Apr. 1990;137(4):1191-2.

Whittingham, Lithium Batteries and Cathode Materials. Chemical Reviews. 2004;104(10):4271-302. Epub Sep. 14, 2004.

Wohfahrt-Mehrens et al., Aging mechanisms of lithium cathode materials. Journal of Power Sources. Mar. 10, 2004;127(1-2):58-64.

Zhang et al., LiBOB-based gel electrolyte Li-ion battery for high temperature operation. Journal of Power Sources. 2006;154:276-80. Epub May 31, 2005.

Zhu et al., Positive Electrode Passivation by LiDFOB Electrolyte Additive in High-Capacity Lithium-Ion Cells. Journal of the Electrochemical Society. 2012;159(12):A2109-17. Epub Oct. 20, 2012.

ADDITIVES FOR ELECTROCHEMICAL CELLS

RELATED APPLICATIONS

This application is a continuation of U.S. application Ser. No. 16/742,340, filed Jan. 14, 2020, which is a continuation of U.S. application Ser. No. 16/299,247 (now U.S. Pat. No. 10,541,448), filed Mar. 12, 2019, which is a continuation of U.S. application Ser. No. 15/349,140 (now U.S. Pat. No. 10,320,031), filed Nov. 11, 2016, which claims priority to U.S. Provisional Application No. 62/254,818, filed Nov. 13, 2015, each of which is incorporated herein by reference in its entirety.

FIELD

Articles and methods involving electrochemical cells including additives are generally provided.

BACKGROUND

There has been considerable interest in recent years in developing high energy density batteries with lithium-containing anodes. In such cells, cathode active material reduction and oxidation electrochemical processes generally involve lithium ions. In particular, cathode active materials may electrochemically intercalate lithium ions and/or produce soluble and insoluble lithium compounds during the charge-discharge process. Rechargeable batteries with such metallic lithium electrodes generally exhibit limited cycle lifetimes. Accordingly, articles and methods for increasing the cycle lifetime and/or other improvements would be beneficial.

SUMMARY

Articles and methods including additives in electrochemical cells, are generally provided. The subject matter disclosed herein involves, in some cases, interrelated products, alternative solutions to a particular problem, and/or a plurality of different uses of one or more systems and/or articles.

In one aspect, electrochemical cells are provided. In some embodiments, an electrochemical cell comprises a first electrode, a second electrode, an electrolyte positioned between the first electrode and the second electrode, an additive having a structure as in Formula (I) and/or an additive precursor having a structure as in Formula (II):

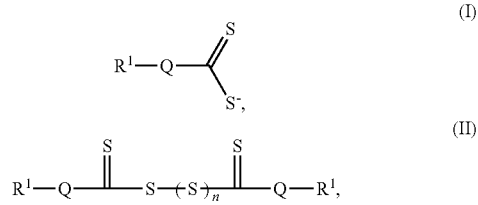

wherein each occurrence of Q is independently selected from the group consisting of Se, O, S, $PR^2$, $CR^2_2$, and $SiR^2_2$, n is 1-6, and each $R^1$ and $R^2$ can be the same or different, optionally connected, and are independently selected from the group consisting of hydrogen, oxygen, sulfur, halogen, nitrogen, phosphorus, substituted or unsubstituted, branched or unbranched aliphatic, substituted or unsubstituted cyclic, substituted or unsubstituted, branched or unbranched acyclic, substituted or unsubstituted, branched or unbranched heteroaliphatic, substituted or unsubstituted, branched or unbranched acyl, substituted or unsubstituted aryl, and substituted or unsubstituted heteroaryl.

In some embodiments, the electrochemical cell comprises a first electrode, a second electrode, an electrolyte positioned between the first electrode and the second electrode, an additive having a structure as in Formula (I) and/or an additive precursor having a structure as in Formula (II):

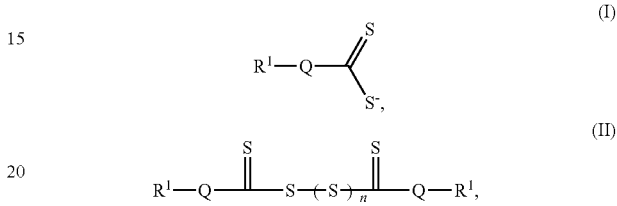

wherein each occurrence of Q is independently selected from the group consisting of Se, O, S, $PR^2$, $NR^2$, $CR^2_2$, and $SiR^2_2$, n is 1-6, each $R^1$ and $R^2$ can be the same or different, optionally connected, and are independently selected from the group consisting of hydrogen, oxygen, sulfur, halogen, nitrogen, phosphorus, substituted or unsubstituted, branched or unbranched aliphatic, substituted or unsubstituted cyclic, substituted or unsubstituted, branched or unbranched acyclic, substituted or unsubstituted, branched or unbranched heteroaliphatic, substituted or unsubstituted, branched or unbranched acyl, substituted or unsubstituted aryl, and substituted or unsubstituted heteroaryl, and the additive and any additive precursor is present in the electrochemical cell in a total amount of less than or equal to about 20 wt % versus the total weight of the electrolyte and additive and/or additive precursor, or the additive and any additive precursor is present in the electrochemical cell in a total amount of less than or equal to about 4 wt % versus the weight of each of the first and second electrodes.

In some embodiments, an electrochemical cell comprises a first electrode comprising a first active electrode species, a second electrode comprising a second active electrode species, an electrolyte positioned between the first electrode and the second electrode, an additive having a structure as in Formula (I) and/or an additive precursor having a structure as in Formula (II):

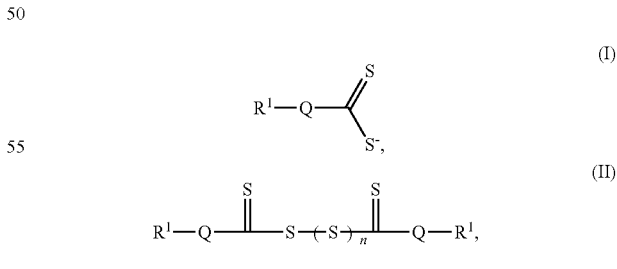

wherein each occurrence of Q is independently selected from the group consisting of Se, O, S, $PR^2$, $NR^2$, $CR^2_2$, and $SiR^2_2$, n is 1-6, each $R^1$ and $R^2$ can be the same or different, optionally connected, and are independently selected from the group consisting of hydrogen, oxygen, sulfur, halogen, nitrogen, phosphorus, substituted or unsubstituted, branched or unbranched aliphatic, substituted or unsubstituted cyclic, substituted or unsubstituted, branched or unbranched acyclic, substituted or unsubstituted, branched or unbranched heteroaliphatic, substituted or unsubstituted, branched or unbranched acyl, substituted or unsubstituted aryl, and substituted or unsubstituted heteroaryl, and wherein the additive and any additive precursor is/are different from the first and second active electrode species.

In some embodiments, an electrochemical cell comprises a first electrode comprising a first active electrode species, a second electrode comprising a second active electrode species, an electrolyte positioned between the first electrode and the second electrode, lithium bis-oxalatoborate, and an additive having a structure as in Formula (I):

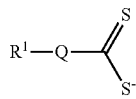

(I)

wherein each occurrence of Q is independently selected from the group consisting of Se, O, S, $PR^2$, $NR^2$, $CR^2_2$, and $SiR^2_2$, each $R^1$ and $R^2$ can be the same or different, optionally connected, and are independently selected from the group consisting of hydrogen, oxygen, sulfur, halogen, nitrogen, phosphorus, substituted or unsubstituted, branched or unbranched aliphatic, substituted or unsubstituted cyclic, substituted or unsubstituted, branched or unbranched acyclic, substituted or unsubstituted, branched or unbranched heteroaliphatic, substituted or unsubstituted, branched or unbranched acyl, substituted or unsubstituted aryl, and substituted or unsubstituted heteroaryl, and wherein the additive and any additive precursor is/are different from the first and second active electrode species.

In some embodiments, an electrochemical cell comprises a first electrode comprising a first active electrode species, a second electrode comprising a second active electrode species, an electrolyte positioned between the first electrode and the second electrode, lithium bis-oxalatoborate and one or more of an ethyl xanthate salt, a diethiocarbamate salt, and an isopropyl xanthate salt.

In some embodiments, an electrochemical cell comprises a first electrode comprising a first active electrode species, a second electrode comprising a second active electrode species, an electrolyte positioned between the first electrode and the second electrode, lithium bis-oxalatoborate, and an additive having a structure as in Formula (I):

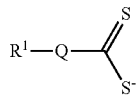

(I)

wherein each occurrence of Q is independently selected from the group consisting of Se, O, S, $PR^2$, $NR^2$, $CR^2_2$, and $SiR^2_2$, each $R^1$ and $R^2$ can be the same or different, optionally connected, and are independently selected from the group consisting of hydrogen, oxygen, sulfur, halogen, nitrogen, phosphorus, substituted or unsubstituted, branched or unbranched aliphatic, substituted or unsubstituted cyclic, substituted or unsubstituted, branched or unbranched acyclic, substituted or unsubstituted, branched or unbranched heteroaliphatic, substituted or unsubstituted, branched or unbranched acyl, substituted or unsubstituted aryl, and substituted or unsubstituted heteroaryl, and wherein the additive and any additive precursor is/are different from the first and second active electrode species. The second electrode is an intercalation electrode (e.g., a lithium intercalation electrode), optionally comprising one or more of $Li_xCoO_2$, $Li_xNiO_2$, $Li_xMnO_2$, $Li_xMn_2O_4$, $Li_xFePO_4$, $Li_xCoPO_4$, $Li_xMnPO_4$, and $Li_xNiPO_4$, where ($0<x\leq1$), and $LiNi_xMny\text{-}Co_zO_2$ where ($x+y+z=1$).

In another aspect, methods are provided. In some embodiments, a method comprises introducing into an electrochemical cell an additive having a structure as in Formula (I) and/or an additive precursor having a structure as in Formula (II):

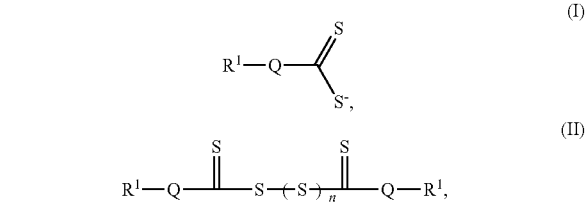

wherein each occurrence of Q is independently selected from the group consisting of Se, O, S, $NR^2$, $PR^2$, $CR^2_2$, and $SiR^2_2$, n is 1-6, each $R^1$ and $R^2$ can be the same or different, optionally connected, and are independently selected from the group consisting of hydrogen, oxygen, sulfur, halogen, nitrogen; phosphorus; substituted or unsubstituted, branched or unbranched aliphatic, substituted or unsubstituted cyclic, substituted or unsubstituted, branched or unbranched acyclic, substituted or unsubstituted, branched or unbranched heteroaliphatic, substituted or unsubstituted, branched or unbranched acyl, substituted or unsubstituted aryl, and substituted or unsubstituted heteroaryl, and wherein the electrode comprises active electrode species that is/are different from the additive and any additive precursor.

In some embodiments, a method comprises introducing into an electrochemical cell or a component of an electrochemical cell an additive having a structure as in Formula (I) and/or an additive precursor having a structure as in Formula (II):

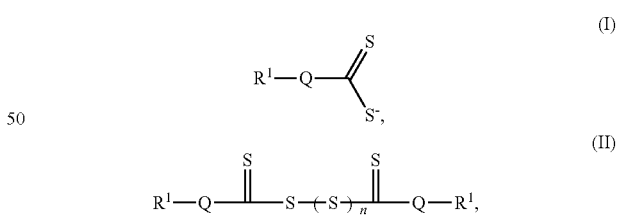

wherein each occurrence of Q is independently selected from the group consisting of Se, O, S, $PR^2$, $CR^2_2$, and $SiR^2_2$, n is 1-6, and each $R^1$ and $R^2$ can be the same or different, optionally connected, and are independently selected from the group consisting of hydrogen, oxygen, sulfur, halogen, nitrogen, phosphorus, substituted or unsubstituted, branched or unbranched aliphatic, substituted or unsubstituted cyclic, substituted or unsubstituted, branched or unbranched acyclic, substituted or unsubstituted, branched or unbranched heteroaliphatic, substituted or unsubstituted, branched or unbranched acyl, substituted or unsubstituted aryl, and substituted or unsubstituted heteroaryl.

In certain embodiments involving the methods described above and herein, an introducing step comprises adding to an electrolyte the additive having a structure as in Formula (I) and/or the additive precursor having a structure as in Formula (II). In certain embodiments involving the methods described above and herein, an introducing step comprises applying a coating to at least a portion of a surface of an electrode, the coating comprises the additive having a structure as in Formula (I) and/or the additive precursor having a structure as in Formula (II).

In certain embodiments involving the electrochemical cells and/or methods described above and herein, the electrochemical cell comprises a first electrode comprising a first active electrode species and a second electrode comprising a second active electrode species, wherein the first and second active electrode species are different from the additive and the additive precursor.

In certain embodiments involving the electrochemical cells and/or methods described above and herein, the additive and/or additive precursor is polyanionic and/or a salt.

In certain embodiments involving the electrochemical cells and/or methods described above and herein, the additive comprises a cation selected from the group consisting of $Li^+$, $Na^+$, $K^+$, $Cs^+$, $Rb^+$, $Ca^{+2}$, $Mg^{+2}$, substituted or unsubstituted ammonium, guanidinium and imidazolium.

In certain embodiments involving the electrochemical cells and/or methods described above and herein, the additive and/or additive precursor comprises a xanthate group.

In certain embodiments involving the electrochemical cells and/or methods described above and herein, each $R^1$ is $C_2H_5$ and/or each $R^2$ is $C_2H_5$.

In certain embodiments involving the electrochemical cells and/or methods described above and herein, Q is oxygen or sulfur.

In certain embodiments involving the electrochemical cells and/or methods described above and herein, $n=1$.

In certain embodiments involving the electrochemical cells and/or methods described above and herein, at least a portion of the additive and/or additive precursor is in solid form.

In certain embodiments involving the electrochemical cells and/or methods described above and herein, at least a portion of the additive and/or additive precursor is dissolved in the electrolyte.

In certain embodiments involving the electrochemical cells and/or methods described above and herein, the additive and/or additive precursor is at least partially soluble in the electrolyte.

In certain embodiments involving the electrochemical cells and/or methods described above and herein, the additive and/or additive precursor is disposed on and/or within the first electrode and/or the second electrode.

In certain embodiments involving the electrochemical cells and/or methods described above and herein, the additive and/or additive precursor is present in the electrolyte.

In certain embodiments involving the electrochemical cells and/or methods described above and herein, the additive and any additive precursor is present in the electrolyte in a total amount ranging between about 0.5 wt % and about 20 wt % versus the total weight of the electrolyte and additive and/or additive precursor.

In certain embodiments involving the electrochemical cells and/or methods described above and herein, the additive and any additive precursor is present in the electrolyte in a total amount ranging between about 0.5 wt % and about 10 wt % versus the weight of each of the first and second electrodes.

In certain embodiments involving the electrochemical cells and/or methods described above and herein, the additive and/or additive precursor is disposed on and/or within a separator positioned between the first electrode and the second electrode.

In certain embodiments involving the electrochemical cells and/or methods described above and herein, the additive and/or additive precursor is present in a reservoir positioned between the first electrode and the second electrode.

In certain embodiments involving the electrochemical cells and/or methods described above and herein, the electrolyte comprises a nitrate selected from the group consisting of $LiNO_3$, guanidine nitrate, and pyridine nitrate.

In certain embodiments involving the electrochemical cells and/or methods described above and herein, the electrolyte comprises one or more of a carbonate, a hexafluorophosphate, 1,3-dioxolane, 1,2-dimethoxyethane, a sulfonimide, sulfones, sulfolanes, esters of carbonic acid, and/or a nitrate containing compound.

In certain embodiments involving the electrochemical cells and/or methods described above and herein, the first active electrode species comprises lithium and/or the second active electrode species comprises sulfur.

In certain embodiments involving the electrochemical cells and/or methods described above and herein, the second electrode is an intercalated electrode.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1A:
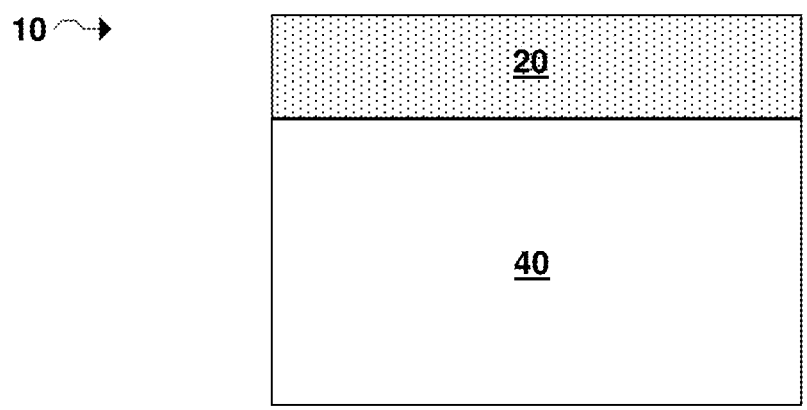
FIGS. 1A-1F are a schematics of articles incorporating additives and/or additive precursors, according to some embodiments.

Articles and methods involving electrochemical cells including additives are generally provided. In some embodiments, an electrochemical cell may include a first electrode, a second electrode, an electrolyte, and optionally a separator. In some embodiments, at least one of the first electrode, second electrode, electrolyte, and/or optional separator may include an additive and/or additive precursor incorporated therein. For instance, in some cases the electrolyte includes an additive such as a carbon disulfide salt and/or an additive precursor that is soluble within the electrolyte and can form the additive upon cycling of the electrochemical cell.

Advantageously, an electrochemical cell comprising one or more additives and/or additive precursors described herein may offer one or more advantages over electrochemical cells that do not include such an additive or additive precursor, including, but not limited to, increasing cycle lifetimes, providing improved lithium morphologies, increasing the compaction of lithium, and/or reducing the depletion of lithium during charge/discharge of an electrochemical cell.

The disclosed additives and additive precursors may be incorporated into various electrochemical cells. In some cases, the electrochemical cell may be a lithium-based electrochemical cell, such as a lithium-sulfur electrochemical cell, a lithium-ion electrochemical cell, a lithium metal-lithium-ion electrochemical cell, an intercalated lithium metal oxide electrochemical cell, an intercalated lithium metal phosphate electrochemical cell.

The additives and/or additive precursors may be included in any suitable form in an electrochemical cell, as described in more detail below. In some embodiments, the additives and/or additive precursors may be added, in some cases, as a solid (e.g., a salt, as particles) incorporated within the cathode, the anode, and/or the optional separator, or in particular embodiments, as a solid layer on the cathode, the anode, and/or the optional separator. In some such embodiments, the solid additive and/or additive precursor may be soluble or partially soluble in the electrolyte. In some cases, upon cycling of the electrochemical cell, the additive or additive precursor may remain in the component to which the additive or additive precursor was originally included (e.g., upon fabrication of electrochemical cell). In other cases, at least a portion of the additive or additive precursor may leach out of the component to which the additive or additive precursor was originally included, and migrate into the electrolyte. In other embodiments, the additive or additive precursor may be included in the electrolyte (e.g., in soluble or partially-soluble form) upon fabrication of the electrochemical cell. Combinations of such configurations is also possible.

In some embodiments, the additive comprises a structure as in Formula (I):

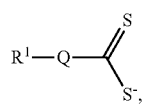

(I)

wherein Q is selected from the group consisting of Se, O, S, $PR^2$, $NR^2$, $CR^2_2$, and $SiR^2_2$, and each $R^1$ and $R^2$ can be the same or different, optionally connected, and are independently selected from the group consisting of hydrogen; oxygen; sulfur; halogen; halide; nitrogen; phosphorus; substituted or unsubstituted, branched or unbranched aliphatic; substituted or unsubstituted cyclic; substituted or unsubstituted, branched or unbranched acyclic; substituted or unsubstituted, branched or unbranched heteroaliphatic; substituted or unsubstituted, branched or unbranched acyl; substituted or unsubstituted aryl; and substituted or unsubstituted heteroaryl.

In certain embodiments, Q is independently selected from the group consisting of Se, O, S, $PR^2$, $CR^2_2$, and $SiR^2_2$, and each $R^1$ and $R^2$ can be the same or different, optionally connected, and are independently selected from the group consisting of hydrogen; oxygen; sulfur; halogen; halide; nitrogen; phosphorus; substituted or unsubstituted, branched or unbranched aliphatic; substituted or unsubstituted cyclic; substituted or unsubstituted, branched or unbranched acyclic; substituted or unsubstituted, branched or unbranched heteroaliphatic; substituted or unsubstituted, branched or unbranched acyl; substituted or unsubstituted aryl; and substituted or unsubstituted heteroaryl.

In certain embodiments, Q is independently selected from the group consisting of Se, O, S, $NR^2$, $PR^2$, $CR^2_2$, and $SiR^2_2$. In a particular embodiment, Q is sulfur. In another embodiment, Q is $NR^2$. In some embodiments, the additive is a xanthate salt comprising a structure as in Formula (I) such that Q is oxygen. In certain embodiments, the additive is a dithiocarbamate salt comprising a structure in Formula (I) such that Q is nitrogen.

In an exemplary embodiment, the additive comprises a structure as in Formula (I) wherein Q is oxygen and $R^1$ is $C_2H_5$. In another exemplary embodiment, the additive comprises a structure as in Formula (I) wherein Q is sulfur and $R^1$ is $C_2H_5$. In yet another exemplary embodiment, the additive comprises a structure as in Formula (I) wherein Q is $NR^2$, and $R^1$ and $R^2$ are each $C_2H_5$.

In certain embodiments, the additive comprising a structure as in Formula (I) further comprises a cation. In certain embodiments, the cation is selected from the group consisting of $Li^+$, $Na^+$, $K^+$, $Cs^+$, $Rb^+$, $Ca^{+2}$, $Mg^{+2}$, substituted or unsubstituted ammonium, and organic cations such as guanidinium or imidazolium. In some cases, the additive may be polyanionic.

In an exemplary embodiment, the additive is potassium ethyl xanthate having a structure as in:

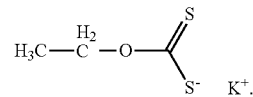

In another exemplary embodiment, the additive is lithium diethyl dithiocarbamate having a structure as in:

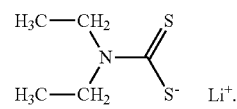

In yet another exemplary embodiment, the additive is potassium isopropyl xanthate having a structure as in:

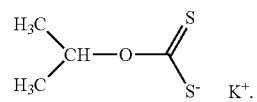

Those skilled in the art would understand that additional structures and cations are also possible based upon the teachings of this specification.

As described herein, in some embodiments, the additive is derived from an additive precursor. In certain embodiments, the electrochemical cell comprises the additive precursor such that, for example, the additive precursor oxidizes into an additive as described herein after being incorporated into the electrochemical cell. For instance, in some embodiments, the additive may form from the additive precursor during charge/discharge of the electrochemical cell. For example, in some cases, the additive precursor may be added to the electrochemical cell (e.g., in the electrolyte, as part of a first or second electrode, as part of a layer in the cell) where at least a portion of the additive precursor forms an additive as described herein.

In some embodiments, the additive precursor comprises a structure as in Formula (II):

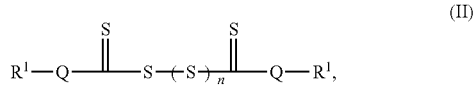

(II)

wherein each Q is independently selected from the group consisting of Se, O, S, $PR^2$, $NR^2$, $CR^2_2$, and $SiR^2_2$, and each $R^1$ and $R^2$ can be the same or different, optionally connected, and are independently selected from the group consisting of hydrogen; oxygen; sulfur; halogen; halide; nitrogen; phosphorus; substituted or unsubstituted, branched or unbranched aliphatic; substituted or unsubstituted cyclic; substituted or unsubstituted, branched or unbranched acyclic; substituted or unsubstituted, branched or unbranched heteroaliphatic; substituted or unsubstituted, branched or unbranched acyl; substituted or unsubstituted aryl; and substituted or unsubstituted heteroaryl. In certain embodiments, each occurrence of Q is independently selected from the group consisting of Se, O, S, $NR^2$, $PR^2$, $CR^2_2$, and $SiR^2_2$.

In some cases, each Q may be the same or different and selected from the group consisting of oxygen, sulfur, and $NR^2$. In a particular embodiment, each Q is the same and is sulfur. In another embodiment, each Q is the same and is $NR^2$. In some embodiments, each Q is the same and is oxygen.

In an exemplary embodiment the additive precursor comprises a structure as in Formula (II) wherein each Q is the same and oxygen and $R^1$ is $C_2H_5$. In another exemplary embodiment, the additive precursor comprises a structure as in Formula (II) wherein each Q is the same and is sulfur and $R^1$ is $C_2H_5$. In yet another exemplary embodiment, the additive precursor comprises a structure as in Formula (II) wherein each Q is the same and is $NR^2$, wherein $R^1$ and $R^2$ are each $C_2H_5$.

In some embodiments, n is 1 (such that the additive precursor comprises a disulfide bridge). In certain embodiments, n is 2-6 (such that the additive precursor comprises a polysulfide). In some cases, n is 1, 2, 3, 4, 5, 6, or combination thereof (e.g., 1-3, 2-4, 3-5, 4-6, 1-4, or 1-6).

In certain embodiments, the additive and any additive precursor is/are different from the first and second active electrode species (e.g., in embodiments in which two electrodes including different active electrode species are present). For example, in some embodiments, the additive having a structure as in Formula (I) and/or the additive precursor having a structure as in Formula (II) is added to an electrochemical cell having a first electrode (e.g., including a first active electrode species comprising lithium metal) and a second electrode (e.g., including a second active electrode species comprising sulfur). In other embodiments, other electroactive species that are not the same species as (or derivatives of) the additive and/or additive precursor can be used. Active electrode species (e.g., anode active electrode species, cathode active electrode species) are described in more detail, below. The addition of additives and additive precursors is also described in more detail, below.

The additive and additive precursor may be present in an electrochemical cell in any suitable amount. The additive and additive precursor may be present, in some cases, in the electrochemical cell in an amount less than or equal to about 20 wt % versus the total weight of the electrolyte and additive and/or additive precursor. For example, in some embodiments, the total weight of the additive and additive precursor present in the electrochemical cell is less than or equal to about 20 wt %, less than or equal to about 18 wt %, less than or equal to about 15 wt %, less than or equal to about 12 wt %, less than or equal to about 10 wt %, less than or equal to about 8 wt %, less than or equal to about 6 wt %, less than or equal to about 5 wt %, less than or equal to about 4 wt %, less than or equal to about 3 wt %, less than or equal to about 2 wt %, or less than or equal to about 1 wt % versus the total weight of the electrolyte and additive and/or additive precursor. In certain embodiments, the total weight of the additive and additive precursor present in the electrochemical cell is greater than about 0.5 wt %, greater than about 1 wt %, greater than about 2 wt %, less than or equal to about 3 wt %, greater than about 4 wt %, greater than about 6 wt %, greater than about 8 wt %, greater than about 10 wt %, or greater than about 15 wt % versus the total weight of the electrolyte and additive and/or additive precursor. Combinations of the above-referenced ranges are also possible (e.g., between about 0.5 wt % and about 20 wt %, between about 1 wt % and about 8 wt %, between about 4 wt % and about 10 wt %, between about 6 wt % and about 15 wt %, between about 8 wt % and about 20 wt %). Other ranges are also possible. In some embodiments, the wt % of additive and additive precursor is measured prior to first use or first discharge of the electrochemical cell. Methods for determining the weight percentage of the additive and additive precursor within the electrolyte are known within the art and may include, in some embodiments, weighing the additive and additive precursor and the electrolyte before adding the additive and/or additive precursor to the electrolyte. In other embodiments, the wt % is measured at a point in time during the cycle life of the cell. In some such embodiments, the cycling of an electrochemical cell may be stopped and the wt % of the electrolyte may be determined using, for example, gas chromatography-mass spectrometry. Other methods such as NMR, inductively coupled plasma mass spectrometry (ICP-MS), and elemental analysis can also be used.

The amount of additive and additive precursor may be measured against the weight of one or more of the first or second electrodes. In some embodiments, the additive and additive precursor may be present in the electrochemical cell in an amount less than or equal to about 10 wt % versus the weight of each of the first and second electrodes. For example, in some embodiments, the total weight of the additive and additive precursor present in the electrochemical cell is less than or equal to about 10 wt %, less than or equal to about 8 wt %, less than or equal to about 6 wt %, less than or equal to about 4 wt %, less than or equal to about 2 wt %, or less than or equal to about 1 wt % versus the weight of each of the first and second electrodes. In certain embodiments, the total weight of the additive and additive precursor present in the electrochemical cell is greater than about 0.5 wt %, greater than about 1 wt %, greater than about 2 wt %, greater than about 4 wt %, greater than about 6 wt %, or greater than about 8 wt % versus the weight of each of the first and second electrodes. Combinations of the above-referenced ranges are also possible (e.g., between about 0.5 wt % and about 10 wt %, between about 1 wt % and about 4 wt %, between about 2 wt % and about 6 wt %, between about 4 wt % and about 8 wt %, between about 6 wt % and about 10 wt %). Other ranges are also possible. In some embodiments, the wt % of additive and additive precursor is measured prior to first use or first discharge of the electrochemical cell. Methods for determining the weight percentage of the additive and additive precursor within a layer (e.g., an electrode, a separator) of the electrochemical cell are known within the art and may include, in some embodiments, weighing the additive and additive precursor and the layer before adding the additive and/or additive precursor to the layer. In other embodiments, the wt % is measured at any point in time during the cycle life of the cell. In some such embodiments, the cycling of an electrochemical cell may be stopped and the wt % of the electrolyte may be determined using, for example, gas chromatography-mass spectrometry. Other methods such as NMR, inductively coupled plasma mass spectrometry (ICP-MS), and elemental analysis can also be used.

While many embodiments described herein relate to lithium-sulfur and/or lithium-ion electrochemical cells, it is to be understood that the additives and/or additive precursors described herein may be used in any suitable electrochemical cell, such as analogous alkali metal/sulfur electrochemical cells (including alkali metal anodes). As noted above and as described in more detail herein, in some embodiments, the additive and/or additive precursor layer is incorporated into an electrochemical cell as a layer adjacent an electrode. In some cases, the electrochemical cell may be fabricated by providing an electrode, an additive layer comprising the additive and/or additive precursor, and an electrolyte layer.

Turning now to the figures, FIG. 1A shows an example of an article that can be incorporated into an electrochemical cell. Article 10 includes an electrode 20 (e.g., an anode or a cathode) that comprises an electroactive material (e.g., lithium metal) and an electrolyte 40 adjacent the electrode. The electrode may include an electroactive material (e.g., an anode active electrode material, a cathode active electrode material). The electrolyte can function as a medium for the storage and transport of ions. The electrolyte may have any suitable configuration such as a liquid electrolyte, a solid electrolyte, or a gel polymer electrolyte, as described in more detail herein. In some embodiments, the additive and/or additive precursor may be at least partially soluble in an electrolyte.

In some embodiments, the additive (e.g., comprising a structure as in Formula (I)) and/or the additive precursor (e.g., comprising a structure as in Formula (II)) may be added to the electrolyte prior or during to formation of the electrochemical cell such that at least a portion (or all) of the additive and/or additive precursor dissolves within the electrolyte. In certain embodiments, the additive and/or additive precursor is added to the electrolyte after formation of the electrochemical cell (e.g., during cycling). For example, the additive and/or additive precursor may initially be a part of a different component of the electrochemical cell (e.g., as part of the anode, cathode, and/or separator), such as upon formation of the electrochemical cell. In some cases, minimal or no amount of the additive and/or additive precursor may be present in the electrolyte at this time. After a certain amount of time and/or upon use (e.g., first use or first discharge, subsequent use) of the electrochemical cell, all or portions of the additive and/or additive precursor may migrate into the electrolyte.

Figure 1B:
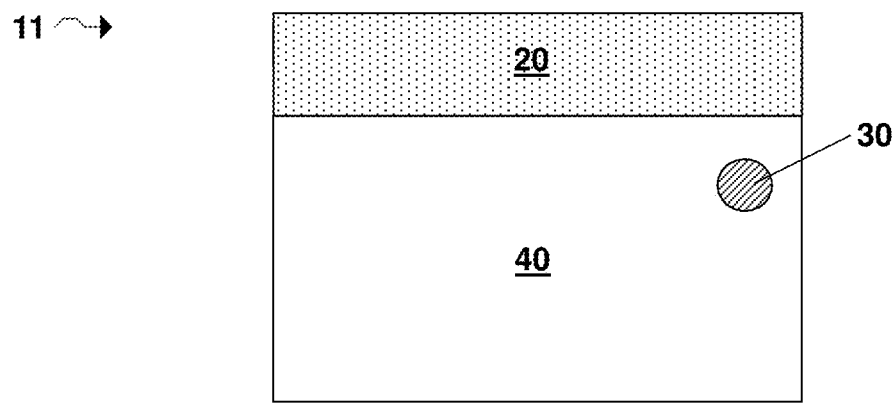

In certain embodiments, at least a portion of (or all of) the additive and/or additive precursor may be in solid form (e.g., as one or more particles or as one or more solid structures) in the electrochemical cell at at least one point in time in the life of the electrochemical cell (e.g., prior to first use or first discharge of the electrochemical cell). In some such embodiments, the solid additive and/or additive precursor may advantageously act as a reservoir of additive such that the additive and/or additive precursor dissolves over time in the electrolyte (e.g., during charge/discharge of the electrochemical cell). For example, as shown illustratively in FIG. 1B, an article 11 includes electrode 20 including an electroactive material, electrolyte 40 adjacent electrode 20, and a reservoir 30 comprising the additive and/or additive precursor. In some cases, the solid additive and/or additive precursor is in the form of a solid particle. For example, in some embodiments, the electrochemical cell comprises a plurality of additive solid particles and/or a plurality of additive precursor solid particles (e.g., in the electrolyte, in an electrode, in a layer, and/or in a separator).

If particles of additives and/or additive precursors are present, the particles may have any suitable size. In some embodiments, an average largest cross-sectional dimension of a plurality of additive and/or additive precursor solid particles may be, for example, less than or equal to 100 microns, less than or equal to about 50 microns, less than or equal to about 25 microns, less than or equal to about 10 microns, less than or equal to about 5 microns, less or equal to about 2 microns, less than or equal to about 1 micron, less than or equal to about 800 nm, less than or equal to about 500 nm, or less than or equal to about 200 nm. In some embodiments, the average largest cross-sectional dimension of the plurality of particles may be greater than or equal to about 100 nm, greater than or equal to about 200 nm, greater than or equal to about 500 nm, greater than or equal to about 800 nm, greater than or equal to about 1 micron, greater than or equal to about 2 microns, greater than or equal to about 5 microns, greater than or equal to about 10 microns, greater than or equal to about 25 microns, or greater than or equal to about 50 microns. Combinations of the above-referenced ranges are also possible (e.g., a largest cross-sectional dimension of less than about 100 microns and greater than about 100 nm).

The average largest cross-sectional dimension of the plurality of particles may be determined, for example, by imaging the particles with a scanning electron microscope (SEM). An image may be acquired at a magnification between about 10× to about 100,000×, depending on the overall dimensions of the plurality of particles. Those skilled in the art would be capable of selecting an appropriate magnification for imaging the sample. The average largest cross-sectional dimension of the plurality of particles can be determined by taking the longest cross-sectional dimension of each particle in the image and averaging the longest cross-sectional dimensions (e.g., averaging the longest cross-sectional dimensions for 50 particles).

Figure 1C:
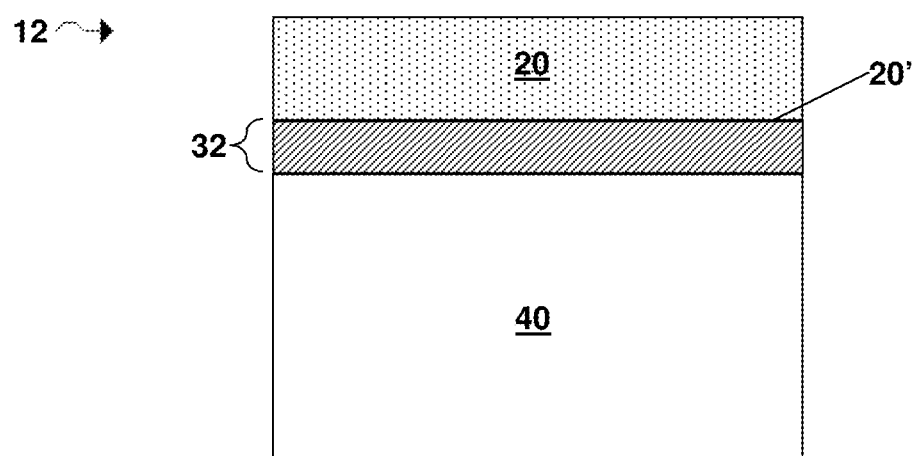

In some embodiments, the additive and/or additive precursor is in solid form and deposited as a layer on or adjacent one or more layers in the electrochemical cell. Referring to FIG. 1C, in some embodiments, an article 12 comprises electrode 20, electrolyte 40 adjacent electrode 20, and an additive layer 32 disposed on or adjacent at least a portion of electrode active surface 20'. As shown illustratively in the figure, the additive layer may be in direct contact with the electrolyte, or one or more intervening layer(s) may be present (not shown). In some embodiments, the additive layer may be adjacent an anode. In some embodiments, the additive layer may be adjacent a cathode. The additive layer can include, for example, the additive and/or the additive precursor and any suitable optional components (e.g., a filler, a polymer, a metal, a ceramic, porous silica sol-gel). In some embodiments, a component included in an additive layer comprises a polymeric binder. Non-limiting examples of suitable polymeric binders include polyethylene oxide, polyethylene, and polyvinylidene fluoride. In certain embodiments, the component (e.g., a component comprising a polymeric binder) may be soluble with and/or may substantially dissolve in an electrolyte. In some cases, the optional component may swell in the presence of an electrolyte.

Figure 1D:
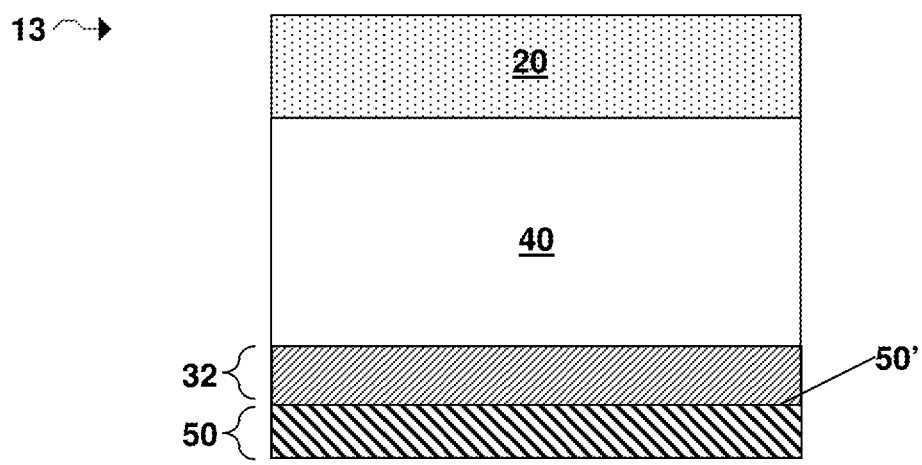

In certain embodiments, the electrochemical cell comprises a separator and the additive layer may be deposited on at least a portion of a surface of the separator, or within the separator. For example, as shown illustratively in FIG. 1D, an article 13 comprises electrode 20, electrolyte 40 adjacent the electrode, and a separator 50 adjacent the electrolyte. In some embodiments, the article comprises an additive layer 32 disposed on at least a portion of separator 50 at separator surface 50'. The additive layer may advantageously serve as a reservoir such that the additive and/or additive precursor dissolves over time in the electrolyte (e.g., during charge/discharge of the electrochemical cell).

Figure 1E:
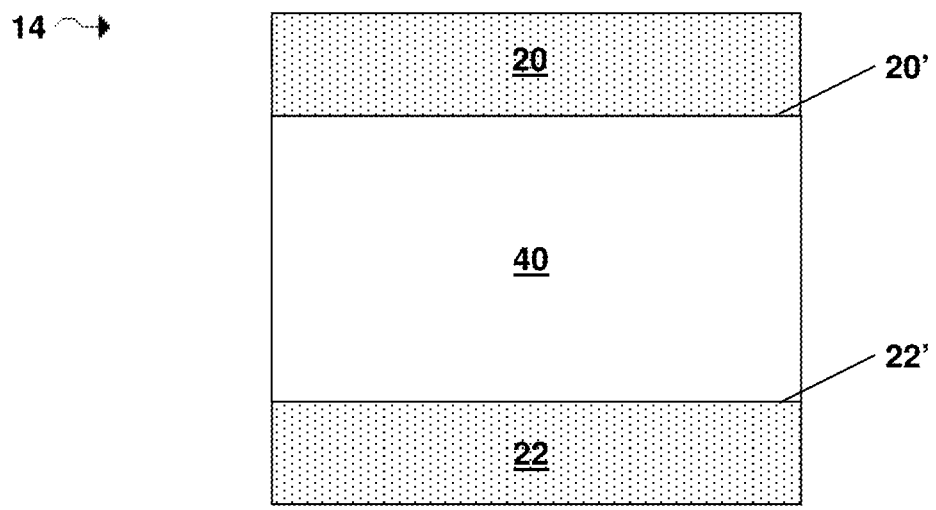

In some cases, the electrochemical cell comprises a first electrode (e.g., an anode), a second electrode (e.g., a cathode), and an electrolyte disposed between the first and second electrodes. For example, as shown illustratively in FIG. 1E, article 14 comprises first electrode 20, second electrode 22, and electrolyte 40 disposed between the first and second electrodes. In some embodiments, the additive and/or additive precursor may be present as a solid additive layer on the first electrode and/or the second electrode, as described herein. In some embodiments, the additive and/or additive precursor may be incorporated into the electrode and/or the separator. For example, the additive and/or additive precursor may be added (e.g., in solid form) to a slurry comprising an electroactive material prior to the formation of an electrode. In some such embodiments, the electrode incorporating the additive and/or additive precursor may serve as a reservoir such that the additive and/or additive precursor dissolves in an electrolyte in contact with the electrode and/or upon use of the electrochemical cell.

A layer referred to as being "disposed on," "disposed between," "on," or "adjacent" another layer(s) means that it can be directly disposed on, disposed between, on, or adjacent the layer(s), or an intervening layer may also be present. For example, an additive layer described herein that is adjacent an anode or cathode may be directly adjacent (e.g., may be in direct physical contact with) the anode or cathode, or an intervening layer (e.g., another protective layer) may be positioned between the anode and the additive layer. A layer that is "directly adjacent," "directly on," or "in contact with," another layer means that no intervening layer is present. It should also be understood that when a layer is referred to as being "disposed on," "disposed between," "on," or "adjacent" another layer(s), it may be covered by, on or adjacent the entire layer(s) or a part of the layer(s).

Figure 1F:
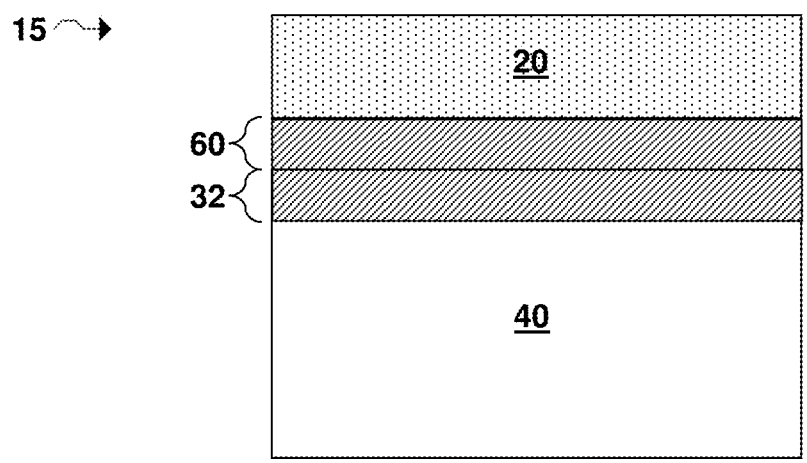

It should be appreciated that FIGS. 1A-1F are exemplary illustrations and that not all components shown in the figure need be present, or, additional components not shown in the figure may be present. For example, an additive layer 32 may be disposed directly on one or more electrodes, or may be disposed on a protective layer in contact with the electrode in some embodiments. In an exemplary embodiment, as shown in FIG. 1F, additive layer 32 may be disposed directly on protective layer 60 which is in direct contact with electrode 20. Other configurations are also possible. Protective layers are described in more detail below.

In some cases, the additive precursor may be added (e.g., as a solid, as a film, dissolved in solution) to an electrolyte, an electrode, a separator, and/or any additional layers of an electrochemical cell in an amount described above, e.g., prior to formation, prior to first use or first discharge, or during use, of the electrochemical cell. In some such embodiments, the additive precursor (e.g., having a structure as in Formula (II)) may react and/or solubilize with the electrolyte such that at least a portion of the additive precursor present in the electrochemical cell forms the additive (e.g., having a structure as in Formula (I)). In some cases, a mixture comprising the additive and the additive precursor may be provided to the electrochemical cell, or a component of an electrochemical cell, as described herein. The ratio of the additive and the additive precursor may be, for example, at least about 1:1000, at least about 1:500, at least about 1:200, at least about 1:100, at least about 1:50, at least about 1:20, at least about 1:10, at least about 1:5, at least about 1:2, at least about 1:1, at least about 2:1, at least about 5:1, at least about 10:1, at least about 20:1, at least about 50:1, at least about 100:1, at least about 200:1, or at least about 500:1. In certain embodiments, the ratio of the additive and the additive precursor may be less than or equal to about 1000:1, less than or equal to about 500:1, less than or equal to about 200:1, less than or equal to about 100:1, less than or equal to about 50:1, less than or equal to about 20:1, less than or equal to about 10:1, less than or equal to about 5:1, less than or equal to about 2:1, less than or equal to about 1:1, less than or equal to about 1:2, less than or equal to about 1:5, less than or equal to about 1:10, less than or equal to about 1:20, less than or equal to about 1:50, less than or equal to about 1:100, less than or equal to about 1:200, or less than or equal to about 1:500. Combinations of the above-referenced ranges are also possible (e.g., at least about 1:1000 and less than or equal to about 1000:1). Other ranges are also possible. In certain embodiments, a mixture comprising the additive with substantially no additive precursor may be provided to the electrochemical cell or component of a cell. In some embodiments, a mixture comprising the additive precursor with substantially no additive may be provided to the electrochemical cell or component of a cell. Methods for determining the ratio of the additive and additive are known within the art and may include, in some embodiments, weighing the additive and additive precursor before mixing the additive and/or additive precursor. In other embodiments, the ratio is measured at a point in time during the cycle life of the cell. In some such embodiments, the cycling of an electrochemical cell may be stopped and the ratio is determined by measuring the wt % of the additive and the wt % of the additive precursor using gas chromatography-mass spectrometry. Other methods are also possible as described herein.

The additive and/or additive precursor may be deposited on one or more layers of an electrochemical cell (e.g., an anode, a cathode, a separator, a protective layer) using any suitable method. Non-limiting examples of suitable methods for depositing the additive and/or additive precursor on a layer of the electrochemical cell include vacuum sputtering, thermal evaporation, solution coating, wet spraying, dry spraying, aerosol deposition, vacuum deposition, particle electrostatic deposition, solvent evaporation, and the like. In an exemplary embodiment, the additive and/or additive precursor may be mixed with a solvent (and/or other materials such as a filler, a polymer, a metal, a ceramic) and coated on a layer of the electrochemical cell (such as an electrode). The coating may be dried, in some such embodiments, such that the additive and/or additive precursor is in solid form thereby forming an additive layer.

The additive layer, if present, may have any suitable thickness. In some embodiments, the additive layer (e.g., comprising the additive and/or additive precursor) described herein may have a thickness of at least about 10 nm at least about 20 nm, at least about 50 nm, at least about 100 nm, at least about 200 nm, at least about 500 nm, at least about 1 micron, at least about 5 microns, at least about 10 microns, at least about 15 microns, at least about 20 microns, at least about 25 microns, at least about 30 microns, at least about 40 microns, at least about 50 microns, at least about 70 microns, at least about 100 microns, at least about 200 microns, at least about 500 microns, or at least about 1 mm. In some embodiments, the thickness of the additive layer is less than or equal to about 1 mm, less than or equal to about 500 microns, less than or equal to about 200 microns, less than or equal to about 100 microns, less than or equal to about 70 microns, less than or equal to about 50 microns, less than or equal to about 40 microns, less than or equal to about 30 microns, less than or equal to about 20 microns, less than or equal to about 10 microns, less than or equal to about 5 microns, less than or equal to about 1 micron, less than or equal to about 500 nm, less than or equal to about 200 nm, less than or equal to about 100 nm, less than or equal to about 50 nm, or less than or equal to about 20 nm. Other values are also possible. Combinations of the above-noted ranges are also possible.

The average thickness of the additive layer can be determined by, for example, using a drop gauge or scanning electron microscopy (SEM). Briefly, the additive layer can be imaged along a cross-section (e.g., by cutting the additive layer) after formation and the image may be acquired by SEM. The average thickness may be determined by taking an average of the thickness of the sample at several different locations along the cross-section (e.g., at least 5 locations). Those skilled in the art would be capable of selecting an appropriate magnification for imaging the sample.

As described herein, an electrochemical cell or an article for use in an electrochemical cell may include an electrode comprising an active electrode species. In some embodiments, a first electrode described herein comprises a first active electrode species. In some cases, the first layer may be an anode (e.g., an anode of an electrochemical cell). In some embodiments, an additive layer comprising the additive and/or additive precursor is deposited on an anode. In certain embodiments, the additive and/or additive precursor is incorporated into the electrode (e.g., by mixing with an active electrode material prior to the formation of the anode).

Suitable active electrode materials for use as anode active electrode species in the electrochemical cells described herein include, but are not limited to, lithium metal such as lithium foil and lithium deposited onto a conductive substrate, and lithium alloys (e.g., lithium-aluminum alloys and lithium-tin alloys). Lithium can be contained as one film or as several films, optionally separated by a protective material such as a ceramic material or an ion conductive material described herein. Suitable ceramic materials include silica, alumina, or lithium containing glassy materials such as lithium phosphates, lithium aluminates, lithium silicates, lithium phosphorous oxynitrides, lithium tantalum oxide, lithium aluminosulfides, lithium titanium oxides, lithium silcosulfides, lithium germanosulfides, lithium aluminosulfides, lithium borosulfides, and lithium phosphosulfides, and combinations of two or more of the preceding. Suitable lithium alloys for use in the embodiments described herein can include alloys of lithium and aluminum, magnesium, silicium (silicon), indium, and/or tin. While these materials may be preferred in some embodiments, other cell chemistries are also contemplated. In some embodiments, the anode may comprise one or more binder materials (e.g., polymers, etc.).

In some embodiments, the thickness of the anode may vary from, e.g., about 2 to 200 microns. For instance, the anode may have a thickness of less than 200 microns, less than 100 microns, less than 50 microns, less than 25 microns, less than 10 microns, or less than 5 microns. In certain embodiments, the anode may have a thickness of greater than or equal to about 2 microns, greater than or equal to about 5 microns, greater than or equal to about 10 microns, greater than or equal to about 25 microns, greater than or equal to about 50 microns, greater than or equal to about 100 microns, or greater than or equal to about 150 microns. Combinations of the above-referenced ranges are also possible (e.g., between about 2 microns and about 200 microns, between about 2 microns and about 100 microns, between about 5 microns and about 50 microns, between about 5 microns and about 25 microns, between about 10 microns and about 25 microns). Other ranges are also possible. The choice of the thickness may depend on cell design parameters such as the excess amount of lithium desired, cycle life, and the thickness of the cathode electrode.

In some embodiments, an electrode described herein may be a cathode (e.g., a cathode of an electrochemical cell). For instance, in some embodiments, an additive layer comprising the additive and/or additive precursor is deposited on a cathode. In certain embodiments, the additive and/or additive precursor is incorporated into the cathode (e.g., by mixing with an cathode active electrode material prior to the formation of the cathode).

Suitable active electrode materials for use as cathode active electrode species in the cathode of the electrochemical cells described herein may include, but are not limited to, electroactive transition metal chalcogenides, electroactive conductive polymers, sulfur, carbon, and/or combinations thereof. As used herein, the term "chalcogenides" pertains to compounds that contain one or more of the elements of oxygen, sulfur, and selenium. Examples of suitable transition metal chalcogenides include, but are not limited to, the electroactive oxides, sulfides, and selenides of transition metals selected from the group consisting of Mn, V, Cr, Ti, Fe, Co, Ni, Cu, Y, Zr, Nb, Mo, Ru, Rh, Pd, Ag, Hf, Ta, W, Re, Os, and Ir. In one embodiment, the transition metal chalcogenide is selected from the group consisting of the electroactive oxides of nickel, manganese, cobalt, and vanadium, and the electroactive sulfides of iron. In certain embodiments, the cathode may include as an electroactive species elemental sulfur, sulfides, and/or polysulfides. In other embodiments, an intercalation electrode (e.g., a lithium-intercalation cathode) may be used. Non-limiting examples of suitable materials that may intercalate ions of an electroactive material (e.g., alkaline metal ions) include oxides, titanium sulfide, and iron sulfide. Additional examples include $Li_xCoO_2$, $Li_xNiO_2$, $Li_xMnO_2$, $Li_xMn_2O_4$, $Li_xFePO_4$, $Li_xCoPO_4$, $Li_xMnPO_4$, and $Li_xNiPO_4$, where ($0<x\leq1$), and $LiNi_xMn_yCo_zO_2$ where ($x+y+z=1$).

In one embodiment, a cathode includes one or more of the following materials: manganese dioxide, iodine, silver chromate, silver oxide and vanadium pentoxide, copper oxide, copper oxyphosphate, lead sulfide, copper sulfide, iron sulfide, lead bismuthate, bismuth trioxide, cobalt dioxide, copper chloride, manganese dioxide, and carbon. In another embodiment, the cathode active layer comprises an electroactive conductive polymer. Examples of suitable electroactive conductive polymers include, but are not limited to, electroactive and electronically conductive polymers selected from the group consisting of polypyrroles, polyanilines, polyphenylenes, polythiophenes, and polyacetylenes. Examples of conductive polymers include polypyrroles, polyanilines, and polyacetylenes.

In some embodiments, active electrode materials for use as cathode active materials in electrochemical cells described herein include electroactive sulfur-containing materials (e.g., lithium-sulfur electrochemical cells). "Electroactive sulfur-containing materials," as used herein, relates to cathode active materials which comprise the element sulfur in any form, wherein the electrochemical activity involves the oxidation or reduction of sulfur atoms or moieties. The nature of the electroactive sulfur-containing materials useful in the practice of this invention may vary widely, as known in the art. For example, in one embodiment, the electroactive sulfur-containing material comprises elemental sulfur. In another embodiment, the electroactive sulfur-containing material comprises a mixture of elemental sulfur and a sulfur-containing polymer. Thus, suitable electroactive sulfur-containing materials may include, but are not limited to, elemental sulfur and organic materials comprising sulfur atoms and carbon atoms, which may or may not be polymeric. Suitable organic materials include those further comprising heteroatoms, conductive polymer segments, composites, and conductive polymers.

In certain embodiments, the sulfur-containing material (e.g., in an oxidized form) comprises a polysulfide moiety, Sm, selected from the group consisting of covalent Sm moieties, ionic Sm moieties, and ionic $Sm_2$-moieties, wherein m is an integer equal to or greater than 3. In some embodiments, m of the polysulfide moiety Sm of the sulfur-containing polymer is an integer equal to or greater than 6 or an integer equal to or greater than 8. In some cases, the sulfur-containing material may be a sulfur-containing polymer. In some embodiments, the sulfur-containing polymer has a polymer backbone chain and the polysulfide moiety Sm is covalently bonded by one or both of its terminal sulfur atoms as a side group to the polymer backbone chain. In certain embodiments, the sulfur-containing polymer has a polymer backbone chain and the polysulfide moiety Sm is incorporated into the polymer backbone chain by covalent bonding of the terminal sulfur atoms of the polysulfide moiety.

In some embodiments, the electroactive sulfur-containing material comprises more than 50% by weight of sulfur. In certain embodiments, the electroactive sulfur-containing material comprises more than 75% by weight of sulfur (e.g., more than 90% by weight of sulfur).

As will be known by those skilled in the art, the nature of the electroactive sulfur-containing materials described herein may vary widely. In some embodiments, the electroactive sulfur-containing material comprises elemental sulfur. In certain embodiments, the electroactive sulfur-containing material comprises a mixture of elemental sulfur and a sulfur-containing polymer.

In certain embodiments, an electrochemical cell as described herein, comprises one or more cathodes comprising sulfur as a cathode active electrode species. In some such embodiments, the cathode includes elemental sulfur as a cathode active electrode species. In some embodiments, the additive is chosen such that the additive is different from the anode active electrode species and different from the cathode active electrode species. In certain embodiments, the additive precursor is chosen such that the additive precursor is different from the anode active electrode species and different from the cathode active electrode species.

In some embodiments, the cathode comprises a nitrate or other N—O compound as described in more detail herein.

Referring again to FIG. 1F, an additive layer (e.g., additive layer 32) may be disposed directly on a protective layer (protective layer 60) which is in direct contact with an electrode (electrode 20), or disposed on a protective layer via an intervening layer. In some embodiments, the protective layer is an ion-conductive layer.

In some embodiments, the protective layer or ion conductive layer is a ceramic layer, a glassy layer, or a glassy-ceramic layer, e.g., an ion conducting ceramic/glass conductive to lithium ions. Suitable glasses and/or ceramics include, but are not limited to, those that may be characterized as containing a "modifier" portion and a "network" portion, as known in the art. The modifier may include a metal oxide of the metal ion conductive in the glass or ceramic. The network portion may include a metal chalcogenide such as, for example, a metal oxide or sulfide. For lithium metal and other lithium-containing electrodes, an ion conductive layer may be lithiated or contain lithium to allow passage of lithium ions across it. Ion conductive layers may include layers comprising a material such as lithium nitrides, lithium silicates, lithium borates, lithium aluminates, lithium phosphates, lithium phosphorus oxynitrides, lithium silicosulfides, lithium germanosulfides, lithium oxides (e.g., $Li_2O$, LiO, $LiO_2$, $LiRO_2$, where R is a rare earth metal), lithium lanthanum oxides, lithium titanium oxides, lithium borosulfides, lithium aluminosulfides, and lithium phosphosulfides, and combinations thereof. The selection of the ion conducting material will be dependent on a number of factors including, but not limited to, the properties of electrolyte, additive (and/or additive precursor) and cathode used in the cell.

In one set of embodiments, the ion conductive layer is a non-electroactive metal layer. The non-electroactive metal layer may comprise a metal alloy layer, e.g., a lithiated metal layer especially in the case where a lithium anode is employed. The lithium content of the metal alloy layer may vary from about 0.5% by weight to about 20% by weight, depending, for example, on the specific choice of metal, the desired lithium ion conductivity, and the desired flexibility of the metal alloy layer. Suitable metals for use in the ion conductive material include, but are not limited to, Al, Zn, Mg, Ag, Pb, Cd, Bi, Ga, In, Ge, Sb, As, and Sn. Sometimes, a combination of metals, such as the ones listed above, may be used in an ion conductive material.

The thickness of an ion conductive material layer may vary over a range from about 1 nm to about 10 microns. For instance, the thickness of the ion conductive material layer may be between 1-10 nm thick, between 10-100 nm thick, between 100-1000 nm thick, between 1-5 microns thick, or between 5-10 microns thick. In some embodiments, the thickness of an ion conductive material layer may be, for example, less than or equal to 10 microns, less than or equal to 5 microns, less than or equal to 1000 nm, less than or equal to 500 nm, less than or equal to 250 nm, less than or equal to 100 nm, less than or equal to 50 nm, less than or equal to 25 nm, or less than or equal to 10 nm. In certain embodiments, the ion conductive layer may have a thickness of greater than or equal to 10 nm, greater than or equal to 25 nm, greater than or equal to 50 nm, greater than or equal to 100 nm, greater than or equal to 250 nm, greater than or equal to 500 nm, greater than or equal to 1000 nm, or greater than or equal to 1500 nm. Combinations of the above-referenced ranges are also possible (e.g., a thickness of greater than or equal to 10 nm and less than or equal to 500 nm). Other thicknesses are also possible. In some cases, the ion conductive layer has the same thickness as a polymer layer.

The ion conductive layer may be deposited by any suitable method such as sputtering, electron beam evaporation, vacuum thermal evaporation, laser ablation, chemical vapor deposition (CVD), thermal evaporation, plasma enhanced chemical vacuum deposition (PECVD), laser enhanced chemical vapor deposition, and jet vapor deposition. The technique used may depend on the type of material being deposited, the thickness of the layer, etc.

In some embodiments, the ion conductive material is non-polymeric. In certain embodiments, the ion conductive material is defined in part or in whole by a layer that is highly conductive toward lithium ions (or other ions) and minimally conductive toward electrons. In other words, the ion conductive material may be one selected to allow certain ions, such as lithium ions, to pass across the layer, but to impede electrons, from passing across the layer. In some embodiments, the ion conductive material forms a layer that allows only a single ionic species to pass across the layer (i.e., the layer may be a single-ion conductive layer). In other embodiments, the ion conductive material may be substantially conductive to electrons.

In some embodiments, the protective layer is a polymer layer comprising a polymeric material. Suitable polymer layers for use in electrochemical cells may be, for example, highly conductive towards lithium and minimally conductive towards electrons. Such polymers may include, for example, ionically conductive polymers, sulfonated polymers, and hydrocarbon polymers. The selection of the polymer will be dependent upon a number of factors including the properties of electrolyte, additive, and cathode used in the cell. Suitable ionically conductive polymers include, e.g., ionically conductive polymers known to be useful in solid polymer electrolytes and gel polymer electrolytes for lithium electrochemical cells, such as, for example, polyethylene oxides. Suitable sulfonated polymers include, e.g., sulfonated siloxane polymers, sulfonated polystyrene-ethylene-butylene polymers, and sulfonated polystyrene polymers. Suitable hydrocarbon polymers include, e.g., ethylene-propylene polymers, polystyrene polymers, and the like.

Polymer layers can also include crosslinked polymer materials formed from the polymerization of monomers such as alkyl acrylates, glycol acrylates, polyglycol acrylates, polyglycol vinyl ethers, polyglycol divinyl ethers, and those described in U.S. Pat. No. 6,183,901 to Ying et al. of the common assignee for protective coating layers for separator layers. For example, one such crosslinked polymer material is polydivinyl poly(ethylene glycol). The crosslinked polymer materials may further comprise salts, for example, lithium salts, to enhance ionic conductivity. In one embodiment, the polymer layer comprises a crosslinked polymer.

Other classes polymers that may be suitable for use in a polymer layer include, but are not limited to, polyamines (e.g., poly(ethylene imine) and polypropylene imine (PPI)); polyamides (e.g., polyamide (Nylon), poly(ε-caprolactam) (Nylon 6), poly(hexamethylene adipamide) (Nylon 66)), polyimides (e.g., polyimide, polynitrile, and poly(pyromellitimide-1,4-diphenyl ether) (Kapton)); vinyl polymers (e.g., polyacrylamide, poly(2-vinyl pyridine), poly(N-vinylpyrrolidone), poly(methylcyanoacrylate), poly(ethylcyanoacrylate), poly(butylcyanoacrylate), poly(isobutylcyanoacrylate), poly(vinyl acetate), poly (vinyl alcohol), poly(vinyl chloride), poly(vinyl fluoride), poly(2-vinyl pyridine), vinyl polymer, polychlorotrifluoro ethylene, and poly(isohexylcynaoacrylate)); polyacetals; polyolefins (e.g., poly(butene-1), poly(n-pentene-2), polypropylene, polytetrafluoroethylene); polyesters (e.g., polycarbonate, polybutylene terephthalate, polyhydroxybutyrate); polyethers (poly(ethylene oxide) (PEO), poly(propylene oxide) (PPO), poly(tetramethylene oxide) (PTMO)); vinylidene polymers (e.g., polyisobutylene, poly(methyl styrene), poly(methylmethacrylate) (PMMA), poly(vinylidene chloride), and poly(vinylidene fluoride)); polyaramides (e.g., poly(imino-1,3-phenylene iminoisophthaloyl) and poly(imino-1,4-phenylene iminoterephthaloyl)); polyheteroaromatic compounds (e.g., polybenzimidazole (PBI), polybenzobisoxazole (PBO) and polybenzobisthiazole (PBT)); polyheterocyclic compounds (e.g., polypyrrole); polyurethanes; phenolic polymers (e.g., phenol-formaldehyde); polyalkynes (e.g., polyacetylene); polydienes (e.g., 1,2-polybutadiene, cis or trans-1,4-polybutadiene); polysiloxanes (e.g., poly(dimethylsiloxane) (PDMS), poly(diethylsiloxane) (PDES), polydiphenylsiloxane (PDPS), and polymethylphenylsiloxane (PMPS)); and inorganic polymers (e.g., polyphosphazene, polyphosphonate, polysilanes, polysilazanes). The mechanical and electronic properties (e.g., conductivity, resistivity) of these polymers are known. Accordingly, those of ordinary skill in the art can choose suitable polymers for use in lithium batteries, e.g., based on their mechanical and/or electronic properties (e.g., ionic and/or electronic conductivity), and/or can modify such polymers to be ionically conducting (e.g., conductive towards single ions) and/or electronically conducting based on knowledge in the art, in combination with the description herein. For example, the polymer materials listed above may further comprise salts, for example, lithium salts (e.g., LiSCN, LiBr, LiI, LiClO$_4$, LiAsF$_6$, LiSO$_3$CF$_3$, LiSO$_3$CH$_3$, LiBF$_4$, LiB(Ph)$_4$, LiPF$_6$, LiC(SO$_2$CF$_3$)$_3$, and LiN(SO$_2$CF$_3$)$_2$), to enhance ionic conductivity.

The polymeric materials can be selected or formulated to have suitable physical/mechanical characteristics by, for example, tailoring the amounts of components of polymer blends, adjusting the degree of cross-linking (if any), etc.

As described herein, in some embodiments, an electrochemical cell includes a separator. The separator generally comprises a polymeric material (e.g., polymeric material that does or does not swell upon exposure to electrolyte). In some embodiments, the separator is located between the electrolyte and an electrode (e.g., an anode, a cathode).

In some embodiments, an additive layer comprising the additive and/or additive precursor is deposited on a separator. In certain embodiments, the additive and/or additive precursor is incorporated into the separator.

The separator can be configured to inhibit (e.g., prevent) physical contact between a first electrode and a second electrode, which could result in short circuiting of the electrochemical cell. The separator can be configured to be substantially electronically non-conductive, which can inhibit the degree to which the separator causes short circuiting of the electrochemical cell. In certain embodiments, all or portions of the separator can be formed of a material with a bulk electronic resistivity of at least about $10^4$, at least about $10^5$, at least about $10^{10}$, at least about $10^{15}$, or at least about $10^{20}$ Ohm-meters. Bulk electronic resistivity may be measured at room temperature (e.g., 25 degrees Celsius).

In some embodiments, the separator can be ionically conductive, while in other embodiments, the separator is substantially ionically non-conductive. In some embodiments, the average ionic conductivity of the separator is at least about $10^{-7}$ S/cm, at least about $10^{-6}$ S/cm, at least about $10^{-5}$ S/cm, at least about $10^{-4}$ S/cm, at least about $10^{-2}$ S/cm, at least about $10^{-1}$ S/cm. In certain embodiments, the average ionic conductivity of the separator may be less than or equal to about 1 S/cm, less than or equal to about $10^{-1}$ S/cm, less than or equal to about $10^{-2}$ S/cm, less than or equal to about $10^{-3}$ S/cm, less than or equal to about $10^{-4}$ S/cm, less than or equal to about $10^{-5}$ S/cm, less than or equal to about $10^{-6}$ S/cm, less than or equal to about $10^{-7}$ S/cm, or less than or equal to about $10^{-8}$ S/cm. Combinations of the above-referenced ranges are also possible (e.g., an average ionic conductivity of at least about $10^{-8}$ S/cm and less than or equal to about $10^{-1}$ S/cm). Other ion conductivity is are also possible. Conductivity may be measured at room temperature (e.g., 25 degrees Celsius).

In some embodiments, the average ion conductivity of the separator can be determined by pressing the separator between two copper cylinders at a pressure of up to 3 tons/cm². In certain embodiments, the average ion conductivity (i.e., the inverse of the average resistivity) can be measured at 500 kg/cm² increments using a conductivity bridge (i.e., an impedance measuring circuit) operating at 1 kHz. In some such embodiments, the pressure is increased until changes in average ion conductivity are no longer observed in the sample.

In some embodiments, the separator can be a solid. The separator may be porous to allow an electrolyte solvent to pass through it. In some cases, the separator does not substantially include a solvent (like in a gel), except for solvent that may pass through or reside in the pores of the separator. In other embodiments, a separator may be in the form of a gel.

A separator can be made of a variety of materials. The separator may be polymeric in some instances, or formed of an inorganic material (e.g., glass fiber filter papers) in other instances. Examples of suitable separator materials include, but are not limited to, polyolefins (e.g., polyethylenes, poly(butene-1), poly(n-pentene-2), polypropylene, polytetrafluoroethylene), polyamines (e.g., poly(ethylene imine) and polypropylene imine (PPI)); polyamides (e.g., polyamide (Nylon), poly(ε-caprolactam) (Nylon 6), poly(hexamethylene adipamide) (Nylon 66)), polyimides (e.g., polyimide, polynitrile, and poly(pyromellitimide-1,4-diphenyl ether) (Kapton®) (NOMEX®) (KEVLAR®)); polyether ether ketone (PEEK); vinyl polymers (e.g., polyacrylamide, poly(2-vinyl pyridine), poly(N-vinylpyrrolidone), poly(methylcyanoacrylate), poly(ethylcyanoacrylate), poly(butylcyanoacrylate), poly(isobutylcyanoacrylate), poly(vinyl acetate), poly (vinyl alcohol), poly(vinyl chloride), poly (vinyl fluoride), poly(2-vinyl pyridine), vinyl polymer, polychlorotrifluoro ethylene, and poly(isohexylcynaoacrylate)); polyacetals; polyesters (e.g., polycarbonate, polybutylene terephthalate, polyhydroxybutyrate); polyethers (poly(ethylene oxide) (PEO), poly(propylene oxide) (PPO), poly(tetramethylene oxide) (PTMO)); vinylidene polymers (e.g., polyisobutylene, poly(methyl styrene), poly(methylmethacrylate) (PMMA), poly(vinylidene chloride), and poly(vinylidene fluoride)); polyamides (e.g., poly(imino-1,3-phenylene iminoisophthaloyl) and poly(imino-1,4-phenylene iminoterephthaloyl)); polyheteroaromatic compounds (e.g., polybenzimidazole (PBI), polybenzobisoxazole (PBO) and polybenzobisthiazole (PBT)); polyheterocyclic compounds (e.g., polypyrrole); polyurethanes; phenolic polymers (e.g., phenol-formaldehyde); polyalkynes (e.g., polyacetylene); polydienes (e.g., 1,2-polybutadiene, cis or trans-1,4-polybutadiene); polysiloxanes (e.g., poly(dimethylsiloxane) (PDMS), poly(diethylsiloxane) (PDES), polydiphenylsiloxane (PDPS), and polymethylphenylsiloxane (PMPS)); and inorganic polymers (e.g., polyphosphazene, polyphosphonate, polysilanes, polysilazanes). In some embodiments, the polymer may be selected from poly(n-pentene-2), polypropylene, polytetrafluoroethylene, polyamides (e.g., polyamide (Nylon), poly(ε-caprolactam) (Nylon 6), poly(hexamethylene adipamide) (Nylon 66)), polyimides (e.g., polynitrile, and poly(pyromellitimide-1,4-diphenyl ether) (Kapton®) (NOMEX®) (KEVLAR®)), polyether ether ketone (PEEK), and combinations thereof.

The mechanical and electronic properties (e.g., conductivity, resistivity) of these polymers are known. Accordingly, those of ordinary skill in the art can choose suitable materials based on their mechanical and/or electronic properties (e.g., ionic and/or electronic conductivity/resistivity), and/or can modify such polymers to be ionically conducting (e.g., conductive towards single ions) based on knowledge in the art, in combination with the description herein. For example, the polymer materials listed above and herein may further comprise salts, for example, lithium salts (e.g., LiSCN, LiBr, LiI, LiClO$_4$, LiAsF$_6$, LiSO$_3$CF$_3$, LiSO$_3$CH$_3$, LiBF$_4$, LiB (Ph)$_4$, LiPF$_6$, LiC(SO$_2$CF$_3$)$_3$, and LiN(SO$_2$CF$_3$)$_2$), to enhance ionic conductivity, if desired.

The separator may be porous. In some embodiments, the separator pore size may be, for example, less than 5 microns. In certain embodiments, the separator pore size may be between 50 nm and 5 microns, between 50 nm and 500 nm, between 100 nm and 300 nm, between 300 nm and 1 micron, between 500 nm and 5 microns. In some embodiments, the pore size may be less than or equal to 5 microns, less than or equal to 1 micron, less than or equal to 500 nm, less than or equal to 300 nm, less than or equal to 100 nm, or less than or equal to 50 nm. In some embodiments, the pore size may be greater than 50 nm, greater than 100 nm, greater than 300 nm, greater than 500 nm, or greater than 1 micron. Other values are also possible. Combinations of the above-noted ranges are also possible (e.g., a pore size of less than 300 nm and greater than 100 nm). In certain embodiments, the separator may be substantially non-porous.

As described herein, in certain embodiments, the electrochemical cell comprises an electrolyte. The electrolytes used in electrochemical or battery cells can function as a medium for the storage and transport of ions, and in the special case of solid electrolytes and gel electrolytes, these materials may additionally function as a separator between the anode and the cathode. Any suitable liquid, solid, or gel material capable of storing and transporting ions may be used, so long as the material facilitates the transport of ions (e.g., lithium ions) between the anode and the cathode. The electrolyte is electronically non-conductive to prevent short circuiting between the anode and the cathode. In some embodiments, the electrolyte may comprise a non-solid electrolyte.

In some embodiments, the additive and/or additive precursor is at least partially soluble in the electrolyte. In certain embodiments, the additive and/or additive precursor is substantially soluble in the electrolyte. In some embodiments, the additive and/or additive precursor has a solubility in the electrolyte of at least about 1% (w/w), at least about 2% (w/w), at least about 5% (w/w), at least about 10% (w/w), or at least about 15% (w/w). In certain embodiments, the additive and/or additive precursor has a solubility in the electrolyte of less than or equal to about 20% (w/w), less than or equal to about 15% (w/w), less than or equal to about 10% (w/w), less than or equal to about 5% (w/w), or less than or equal to about 2% (w/w). Combinations of the above-referenced ranges are also possible (e.g., at least about 1% (w/w) and less than or equal to about 20% (w/w)). Other ranges are also possible. Solubility, as used herein, is measured at 25° C. and 1 atm. In some embodiments, an electrolyte is in the form of a layer having a particular thickness. An electrolyte layer may have a thickness of, for example, at least 1 micron, at least 5 microns, at least 10 microns, at least 15 microns, at least 20 microns, at least 25 microns, at least 30 microns, at least 40 microns, at least 50 microns, at least 70 microns, at least 100 microns, at least 200 microns, at least 500 microns, or at least 1 mm. In some embodiments, the thickness of the electrolyte layer is less than or equal to 1 mm, less than or equal to 500 microns, less than or equal to 200 microns, less than or equal to 100 microns, less than or equal to 70 microns, less than or equal to 50 microns, less than or equal to 40 microns, less than or equal to 30 microns, less than or equal to 20 microns, less than or equal to 10 microns, or less than or equal to 50 microns. Other values are also possible. Combinations of the above-noted ranges are also possible.

In some embodiments, the electrolyte includes a non-aqueous electrolyte. Suitable non-aqueous electrolytes may include organic electrolytes such as liquid electrolytes, gel polymer electrolytes, and solid polymer electrolytes. These electrolytes may optionally include one or more ionic electrolyte salts (e.g., to provide or enhance ionic conductivity) as described herein. Examples of useful non-aqueous liquid electrolyte solvents include, but are not limited to, non-aqueous organic solvents, such as, for example, N-methyl acetamide, acetonitrile, acetals, ketals, esters (e.g., esters of carbonic acid), carbonates (e.g., ethylene carbonate, dimethyl carbonate), sulfones, sulfites, sulfolanes, suflonimidies (e.g., bis(trifluoromethane)sulfonimide lithium salt). aliphatic ethers, acyclic ethers, cyclic ethers, glymes, polyethers, phosphate esters (e.g., hexafluorophosphate), siloxanes, dioxolanes, N-alkylpyrrolidones, nitrate containing compounds, substituted forms of the foregoing, and blends thereof. Examples of acyclic ethers that may be used include, but are not limited to, diethyl ether, dipropyl ether, dibutyl ether, dimethoxymethane, trimethoxymethane, 1,2-dimethoxyethane, diethoxyethane, 1,2-dimethoxypropane, and 1,3-dimethoxypropane. Examples of cyclic ethers that may be used include, but are not limited to, tetrahydrofuran, tetrahydropyran, 2-methyltetrahydrofuran, 1,4-dioxane, 1,3-dioxolane, and trioxane. Examples of polyethers that may be used include, but are not limited to, diethylene glycol dimethyl ether (diglyme), triethylene glycol dimethyl ether (triglyme), tetraethylene glycol dimethyl ether (tetraglyme), higher glymes, ethylene glycol divinyl ether, diethylene glycol divinyl ether, triethylene glycol divinyl ether, dipropylene glycol dimethyl ether, and butylene glycol ethers. Examples of sulfones that may be used include, but are not limited to, sulfolane, 3-methyl sulfolane, and 3-sulfolene. Fluorinated derivatives of the foregoing are also useful as liquid electrolyte solvents.

In some cases, mixtures of the solvents described herein may also be used. For example, in some embodiments, mixtures of solvents are selected from the group consisting of 1,3-dioxolane and dimethoxyethane, 1,3-dioxolane and diethyleneglycol dimethyl ether, 1,3-dioxolane and triethyleneglycol dimethyl ether, and 1,3-dioxolane and sulfolane. The weight ratio of the two solvents in the mixtures may range, in some cases, from about 5 wt %:95 wt % to 95 wt %:5 wt %.

Non-limiting examples of suitable gel polymer electrolytes include polyethylene oxides, polypropylene oxides, polyacrylonitriles, polysiloxanes, polyimides, polyphosphazenes, polyethers, sulfonated polyimides, perfluorinated membranes (NAFION resins), polydivinyl polyethylene glycols, polyethylene glycol diacrylates, polyethylene glycol dimethacrylates, derivatives of the foregoing, copolymers of the foregoing, cross-linked and network structures of the foregoing, and blends of the foregoing.

Non-limiting examples of suitable solid polymer electrolytes include polyethers, polyethylene oxides, polypropylene oxides, polyimides, polyphosphazenes, polyacrylonitriles, polysiloxanes, derivatives of the foregoing, copolymers of the foregoing, cross-linked and network structures of the foregoing, and blends of the foregoing.

In some embodiments, the non-aqueous electrolyte comprises at least one lithium salt. For example, in some cases, the at least one lithium salt is selected from the group consisting of $LiNO_3$, $LiPF_6$, $LiBF_4$, $LiClO_4$, $LiAsF_6$, $Li_2SiF_6$, $LiSbF_6$, $LiAlCl_4$, lithium bis-oxalatoborate, $LiCF_3SO_3$, $LiN(SO_2F)_2$, $LiC(CnF_{2n+1}SO_2)_3$, wherein n is an integer in the range of from 1 to 20, and $(C_nF_{2n+1}SO_2)_mXLi$ with n being an integer in the range of from 1 to 20, m being 1 when X is selected from oxygen or sulfur, m being 2 when X is selected from nitrogen or phosphorus, and m being 3 when X is selected from carbon or silicon.

In some embodiments, specific combinations of additives and lithium salts in the electrolyte may be present in an electrochemical cell or component(s) of an electrochemical cell. For example, in some embodiments an electrochemical cell or component(s) of an electrochemical cell may comprise both lithium bis-oxalatoborate and an additive that comprises a structure as in Formula (I):

wherein each occurrence of Q is independently selected from the group consisting of Se, O, S, $PR^2$, $NR^2$, $CR^2_2$, and $SiR^2_2$, each $R^1$ and $R^2$ can be the same or different, optionally connected, and are independently selected from the group consisting of hydrogen, oxygen, sulfur, halogen, nitrogen, phosphorus, substituted or unsubstituted, branched or unbranched aliphatic, substituted or unsubstituted cyclic, substituted or unsubstituted, branched or unbranched acyclic, substituted or unsubstituted, branched or unbranched heteroaliphatic, substituted or unsubstituted, branched or unbranched acyl, substituted or unsubstituted aryl, and substituted or unsubstituted heteroaryl, and wherein the additive and any additive precursor is/are different from the first and second active electrode species. In some embodiments, the additive that comprises a structure as in Formula (I) and lithium bis-oxalatoborate may be present in an electrolyte.

In some embodiments, the electrochemical cell may comprise both lithium bis-oxalatoborate and one or more of an ethyl xanthate salt, a diethiocarbamate salt, and an isopropyl xanthate salt as described herein. In some embodiments, such components may be present in an electrolyte. The electrochemical cell may also include first and second electrodes as described herein.

In some embodiments, the combination of lithium bis-oxalatoborate with an additive comprising a structure as in Formula (I) may be present in an electrochemical cell, wherein the electrochemical cell comprises a first electrode as describe herein (e.g., a lithium-containing electrode) and a second electrode. The second electrode may be an intercalation electrode (e.g., a lithium intercalation electrode) such as $Li_xCoO_2$, $Li_xNiO_2$, $Li_xMnO_2$, $Li_xMn_2O_4$, $Li_xFePO_4$, $Li_xCoPO_4$, $Li_xMnPO_4$, and $Li_xNiPO_4$, where (0<x≤1), and $LiNi_xMn_yCo_zO_2$ where (x+y+z=1). Formula (I) is represented by:

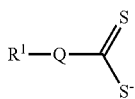

wherein each occurrence of Q is independently selected from the group consisting of Se, O, S, $PR^2$, $NR^2$, $CR^2_2$, and $SiR^2_2$, each $R^1$ and $R^2$ can be the same or different, optionally connected, and are independently selected from the group consisting of hydrogen, oxygen, sulfur, halogen, nitrogen, phosphorus, substituted or unsubstituted, branched or unbranched aliphatic, substituted or unsubstituted cyclic, substituted or unsubstituted, branched or unbranched acyclic, substituted or unsubstituted, branched or unbranched heteroaliphatic, substituted or unsubstituted, branched or unbranched acyl, substituted or unsubstituted aryl, and substituted or unsubstituted heteroaryl, and wherein the additive and any additive precursor is/are different from the first and second active electrode species. In some embodiments, the additive that comprises a structure as in Formula (I) and lithium bis-oxalatoborate may be present in an electrolyte.

In some embodiments, an electrolyte, a cathode, an additive, and/or a component including an additive (e.g. a layer) comprises a nitrate or other N—O compound. Examples of NO compounds include, but are not limited to, families such as inorganic nitrates, organic nitrates, inorganic nitrites, organic nitrites, organic nitro compounds, compounds with negatively, neutral and positively charged $NO_x$ groups, and other organic N—O compounds. Examples of inorganic nitrates that may be used include, but are not limited to, lithium nitrate, potassium nitrate, cesium nitrate, barium nitrate, and ammonium nitrate. Examples of organic nitrates that may be used include, but are not limited to, dialkyl imidazolium nitrates, guanidine nitrate, and pyridine nitrate. Examples of inorganic nitrites that may be used include, but are not limited to, lithium nitrite, potassium nitrite, cesium nitrite, and ammonium nitrite. Examples of organic nitrites that may be used include, but are not limited to, ethyl nitrite, propyl nitrite, butyl nitrite, pentyl nitrite, and octyl nitrite. Examples organic nitro compounds that may be used include, but are not limited to, nitromethane, nitropropane, nitrobutanes, nitrobenzene, dinitrobenzene, nitrotoluene, dinitrotoluene, nitropyridine, and dinitropyridine. Examples of other organic N—O compounds that may be used include, but are not limited to, pyridine N-oxide, alkylpyridine N-oxides, and tetramethyl piperidine N-oxyl (TEMPO). These and other additives are described in more detail in U.S. Pat. No. 7,553,590, entitled "Electrolytes for lithium sulfur cells," which is incorporated herein by reference in its entirety. Electrochemical cells comprising an additive and/or additive precursor described herein and a nitrate may, in some cases, increase the life cycle of electrochemical cells as compared to electrochemical cells without the additive or additive precursor.

In some embodiments, the nitrate or other N—O compound is present in an electrolyte, a cathode, an additive, and/or a component including an additive (e.g. a layer) in an amount of at least about 0.01 wt %, at least about 0.05 wt %, at least about 0.1 wt %, at least about 0.5 wt %, at least about 1 wt %, at least about 2 wt %, at least about 5 wt %, at least about 10 wt %, or at least about 15 wt % versus the total electrolyte weight, total cathode weight, total additive weight, and/or total weight of the component including an additive (e.g., a layer), respectively. In certain embodiments, the nitrate or other N—O compound is present in the electrolyte, a cathode, an additive, and/or a component including an additive (e.g. a layer) in an amount of less than or equal to about 20 wt %, less than or equal to about 15 wt %, less than or equal to about 10 wt %, less than or equal to about 5 wt %, less than or equal to about 2 wt %, less than or equal to about 1 wt %, less than or equal to about 0.5 wt %, less than or equal to about 0.1 wt %, or less than or equal to about 0.05 wt % versus the total electrolyte weight, total cathode weight, total additive weight, and/or total weight of the component including an additive (e.g., a layer), respectively. Combinations of the above-referenced ranges are also possible (e.g., at least about 0.01 wt % and less than or equal to about 20 wt %). Other ranges are also possible.

In some embodiments, an electrochemical cell described herein comprises at least one current collector. Materials for the current collector may be selected, in some cases, from metals (e.g., copper, nickel, aluminum, passivated metals, and other appropriate metals), metallized polymers, electrically conductive polymers, polymers comprising conductive particles dispersed therein, and other appropriate materials. In certain embodiments, the current collector is deposited onto the electrode layer using physical vapor deposition, chemical vapor deposition, electrochemical deposition, sputtering, doctor blading, flash evaporation, or any other appropriate deposition technique for the selected material. In some cases, the current collector may be formed separately and bonded to the electrode structure. It should be appreciated, however, that in some embodiments a current collector separate from the electroactive layer may not be needed.

For convenience, certain terms employed in the specification, examples, and appended claims are listed here. Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito: 1999.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The alkyl groups may be optionally substituted, as described more fully below. Examples of alkyl groups include, but are not limited to, methyl, ethyl, propyl, isopropyl, butyl, isobutyl, tert-butyl, 2-ethylhexyl, cyclopropyl, cyclobutyl, cyclopentyl, cyclohexyl, and the like. "Heteroalkyl" groups are alkyl groups wherein at least one atom is a heteroatom (e.g., oxygen, sulfur, nitrogen, phosphorus, etc.), with the remainder of the atoms being carbon atoms. Examples of heteroalkyl groups include, but are not limited to, alkoxy, poly(ethylene glycol)-, alkyl-substituted amino, tetrahydrofuranyl, piperidinyl, morpholinyl, etc.

The terms "alkenyl" and "alkynyl" refer to unsaturated aliphatic groups analogous to the alkyl groups described above, but containing at least one double or triple bond respectively. The "heteroalkenyl" and "heteroalkynyl" refer to alkenyl and alkynyl groups as described herein in which one or more atoms is a heteroatom (e.g., oxygen, nitrogen, sulfur, and the like).

The term "aryl" refers to an aromatic carbocyclic group having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl), all optionally substituted. "Heteroaryl" groups are aryl groups wherein at least one ring atom in the aromatic ring is a heteroatom, with the remainder of the ring atoms being carbon atoms. Examples of heteroaryl groups include furanyl, thienyl, pyridyl, pyrrolyl, N lower alkyl pyrrolyl, pyridyl N oxide, pyrimidyl, pyrazinyl, imidazolyl, indolyl and the like, all optionally substituted.

The terms "amine" and "amino" refer to both unsubstituted and substituted amines, e.g., a moiety that can be represented by the general formula: N(R')(R")(R'") wherein R', R", and R'" each independently represent a group permitted by the rules of valence.

The terms "acyl," "carboxyl group," or "carbonyl group" are recognized in the art and can include such moieties as can be represented by the general formula:

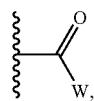

wherein W is H, OH, O-alkyl, O-alkenyl, or a salt thereof. Where W is O-alkyl, the formula represents an "ester." Where W is OH, the formula represents a "carboxylic acid." In general, where the oxygen atom of the above formula is replaced by sulfur, the formula represents a "thiocarbonyl" group. Where W is a S-alkyl, the formula represents a "thiolester." Where W is SH, the formula represents a "thiolcarboxylic acid." On the other hand, where W is alkyl, the above formula represents a "ketone" group. Where W is hydrogen, the above formula represents an "aldehyde" group.

As used herein, the term "heteroaromatic" or "heteroaryl" means a monocyclic or polycyclic heteroaromatic ring (or radical thereof) comprising carbon atom ring members and one or more heteroatom ring members (such as, for example, oxygen, sulfur or nitrogen). Typically, the heteroaromatic ring has from 5 to about 14 ring members in which at least 1 ring member is a heteroatom selected from oxygen, sulfur, and nitrogen. In another embodiment, the heteroaromatic ring is a 5 or 6 membered ring and may contain from 1 to about 4 heteroatoms. In another embodiment, the heteroaromatic ring system has a 7 to 14 ring members and may contain from 1 to about 7 heteroatoms. Representative heteroaryls include pyridyl, furyl, thienyl, pyrrolyl, oxazolyl, imidazolyl, indolizinyl, thiazolyl, isoxazolyl, pyrazolyl, isothiazolyl, pyridazinyl, pyrimidinyl, pyrazinyl, triazinyl, triazolyl, pyridinyl, thiadiazolyl, pyrazinyl, quinolyl, isoquinolyl, indazolyl, benzoxazolyl, benzofuryl, benzothiazolyl, indolizinyl, imidazopyridinyl, isothiazolyl, tetrazolyl, benzimidazolyl, benzoxazolyl, benzothiazolyl, benzothiadiazolyl, benzoxadiazolyl, carbazolyl, indolyl, tetrahydroindolyl, azaindolyl, imidazopyridyl, qunizaolinyl, purinyl, pyrrolo[2,3]pyrimidyl, pyrazolo[3,4]pyrimidyl, benzo(b)thienyl, and the like. These heteroaryl groups may be optionally substituted with one or more substituents.

The term "substituted" is contemplated to include all permissible substituents of organic compounds, "permissible" being in the context of the chemical rules of valence known to those of ordinary skill in the art. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" must still comprise the phenyl moiety and cannot be modified by substitution, in this definition, to become, e.g., a heteroaryl group such as pyridine. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, alkyl, aryl, aralkyl, cyclic alkyl, heterocycloalkyl, hydroxy, alkoxy, aryloxy, perhaloalkoxy, aralkoxy, heteroaryl, heteroaryloxy, heteroarylalkyl, heteroaralkoxy, azido, amino, halogen, alkylthio, oxo, acyl, acylalkyl, carboxy esters, carboxyl, carboxamido, nitro, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, alkoxyalkyl, perhaloalkyl, arylalkyloxyalkyl, and the like.

The following examples are intended to illustrate certain embodiments of the present invention, but do not exemplify the full scope of the invention.

EXAMPLES

In the examples below, an additive was introduced into the electrolyte and resulted in cycle life increases for electrochemical cells having a lithium metal anode/lithium iron phosphate cathode (Examples 1-2) and in Li—S cells in a Beta-2 design (Example 3), and for electrochemical cells having a lithium metal anode/nickel cobalt manganese cathode (Example 4). The weight percentage of the additive was based on the weight of the electrolyte and is listed below. Additive was introduced into two types of electrolytes:
1. EC/DMC $LiPF_6$ (Examples 1-2)
2. DME/DOL+LiTFSI+$LiNO_3$ (Example 3)

The cells were cycled at a normal rate (C/5 discharge and C/8 charge) and at accelerated test conditions: 1C rate discharge and C/3 rate charge.

Example 1

Electrochemical cells were assembled with a lithium iron phosphate cathode received from Enertech (Korea). A vacuum deposited Li anode with thickness of 8.8 um and a Celgard 2325 separator were used. The cathode total active area was 99.441 $cm^2$. Cells were filled with 0.5 ml of three electrolytes:

Electrolyte 1-1: Ethylene Carbonate, 44.1 wt %; Dimethyl Carbonate, 44.1 wt %; $LiPF_6$, 11.8 wt %. (Comparative Electrolyte)

Electrolyte 1-2: 98.5 wt % of Electrolyte 1-1 and 1.5 wt % of Potassium Ethyl Xanthate (additive)

Electrolyte 1-3: 98 wt % of Electrolyte 1-1 and 2 wt % of Lithium Diethyl Dithiocarbamate (additive)

The weight percentage of the additives were based on the total weight of the electrolyte and additive.

Figure 2:
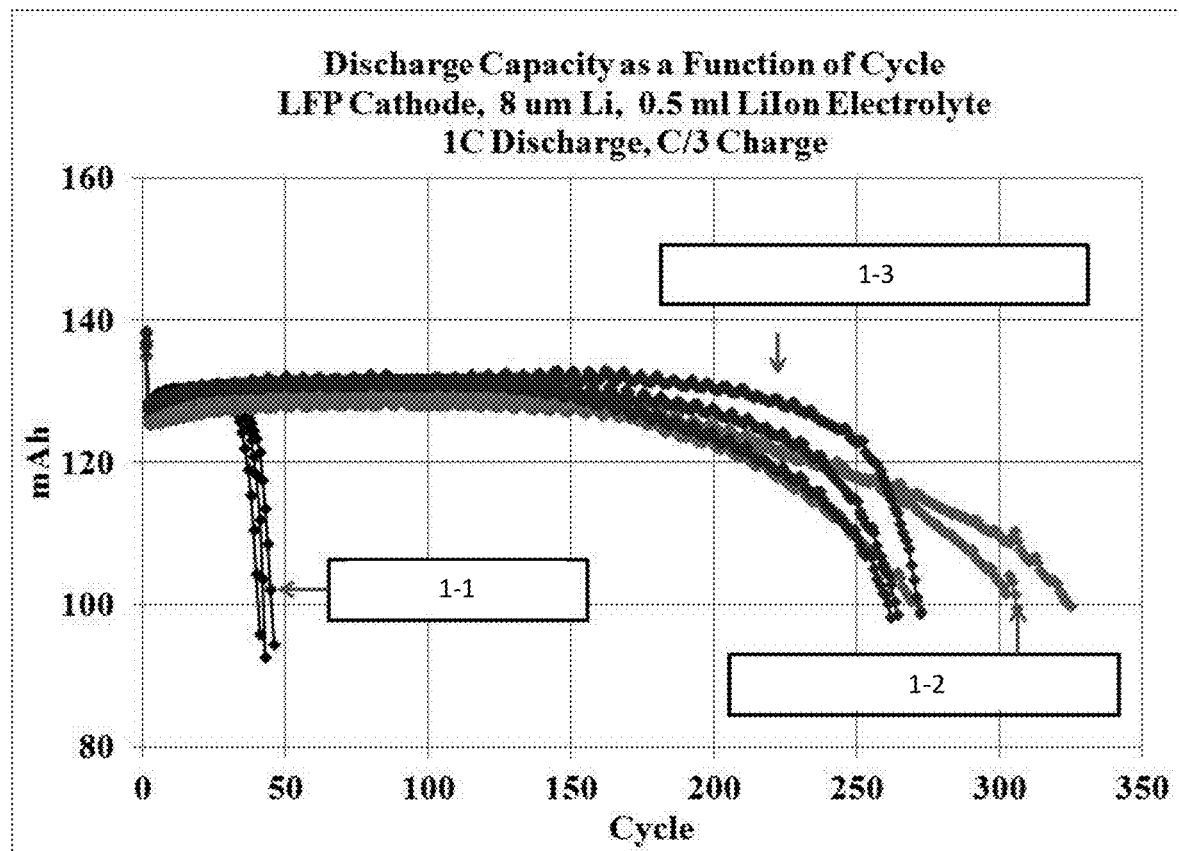
FIGS. 2-5 show plots of cycling behavior of electrochemical cells incorporating additives, according to some embodiments.

Each cell was sealed in the pouch made of Showa Denko packaging material. Cell electrical testing was performed while applying 10 $kg/cm^2$ of anisotropic pressure perpendicular to the electrodes surface. Cells at first cycle were charged at a current of 17 mA to a voltage of 4.2 V and discharged at a current 27 mA to a voltage of 2.5 V. All cells delivered a first cycle discharge capacity of 135-137 mAh. At subsequent cycles the charge current was increased to 45 mA and the discharge current was increased to 137 mA. The cell cycle life was evaluated to the point when discharge capacity dropped below 100 mAh and is shown in FIG. 2. Specifically, cycle life delivered by three electrolytes is listed below:

Electrolyte 1-1: 46 cycles (Comparative Electrolyte)
Electrolyte 1-2: 323 cycles
Electrolyte 1-3: 272 cycles This example shows that the addition of an additive comprising a xanthate or dithiocarbamate to the electrolyte of an electrochemical cell can significantly increase the cycle life of the electrochemical cell.

Example 2

Cells were assembled with Nickel Cobalt Manganese (NCM) cathode received from Enertech (Korea). Vacuum deposited Li anode with thickness of 11 um and a Celgard 2325 separator were used. The cathode total active area was 99.441 $cm^2$. The cells were filled with 0.55 ml of four electrolytes:

Electrolyte 2-1: Ethylene Carbonate 44.1 wt %, Dimethyl Carbonate 44.1 wt %, LiPF6 11.8 w %. (Comparative Electrolyte)

Electrolyte 2-2: 98 wt % of Electrolyte 2-1 and 2 wt % of Potassium Ethyl Xanthate (additive)

Electrolyte 2-3: 98 wt % of Electrolyte 2-1 and 2 wt % of Potassium Isopropyl Xanthate (additive)

Electrolyte 2-4: 98 wt % of Electrolyte 2-1 and 2 wt % of Lithium Diethyl Dithiocarbamate (additive)

The weight percentage of the additive was based on the total weight of the electrolyte and additive.

Each cell was sealed in the pouch made of Showa Denko packaging material. Cells electrical testing was performed while applying 10 $kg/cm^2$ of anisotropic pressure perpendicular to the surface of the electrodes. Cells at the first cycle were charged at a current of 20 mA to a voltage of 4.35 V and discharged at a current of 34 mA to a voltage of 3.2 V. All cells delivered first cycle discharge capacity of 187-190 mAh. At subsequent cycles, the charge current was increased to 57 mA and the discharge current was increased to 170 mA. The cell cycle life was evaluated to the point when discharge capacity dropped below 150 mAh.

Figure 3:
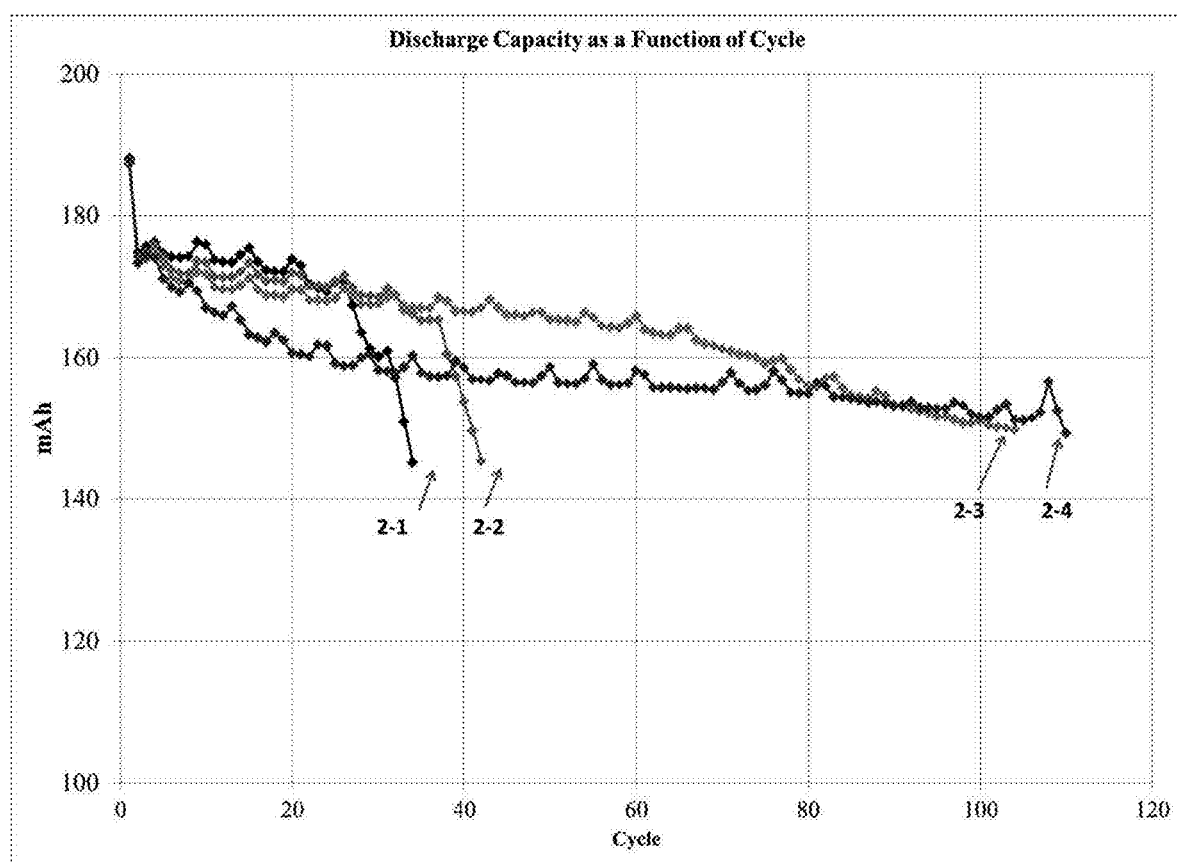

Cycle life delivered by four electrolytes is listed below and shown in FIG. 3:

Electrolyte 2-1: 33 cycles (Comparative Electrolyte)
Electrolyte 2-2: 41 cycle
Electrolyte 2-3: 104 cycles
Electrolyte 2-4: 110 cycles This example shows that the addition of an additive comprising a xanthate or dithiocarbamate to the electrolyte of an electrochemical cell can increase the cycle life of the electrochemical cell.

Example 3

Beta-2 cells, as described here, were assembled with a sulfur cathode coated at Sion Power. The cathode formulation included S-75 wt %, Carbon black-24 wt %, PVOH binder 1 wt %. The sulfur coated loading was of 1.87 $mg/cm^2$. The cells included a Li foil anode with a thickness of 50 um and Tonen separator with thickness of 9 um. Cathode total active area was 1289 $cm^2$. Different cells were filled with 7 g of one of three electrolytes:

Electrolyte 3-1: 1,3-Dioxolane 43.3 wt %, 1,2-Dimethoxyethane 43.3 wt %, LiTFSI 8 w %, $LiNO_3$ 4 wt %, Guanidine Nitrate 1 wt %, Pyridine Nitrate 0.4 wt %. (Comparative Electrolyte)

Electrolyte 3-2: 98 wt % of Electrolyte 3-1 and 2 wt % of Potassium Ethyl Xanthate.

Electrolyte 3-3: 98 wt % of Electrolyte 3-1 and 2 wt % of Potassium Isopropyl Xanthate.

Each cell was sealed in the pouch made of Showa Denko packaging material. Cells were discharged at current 0.5 A to voltage 1.7 V and charged at current 0.315 A to voltage of 2.5 V. All cells delivered fifth cycle discharge capacity of 2.85-2.87 Ah. Cells cycle life was evaluated to the point when discharge capacity dropped below 1.75 Ah.

Figure 4:
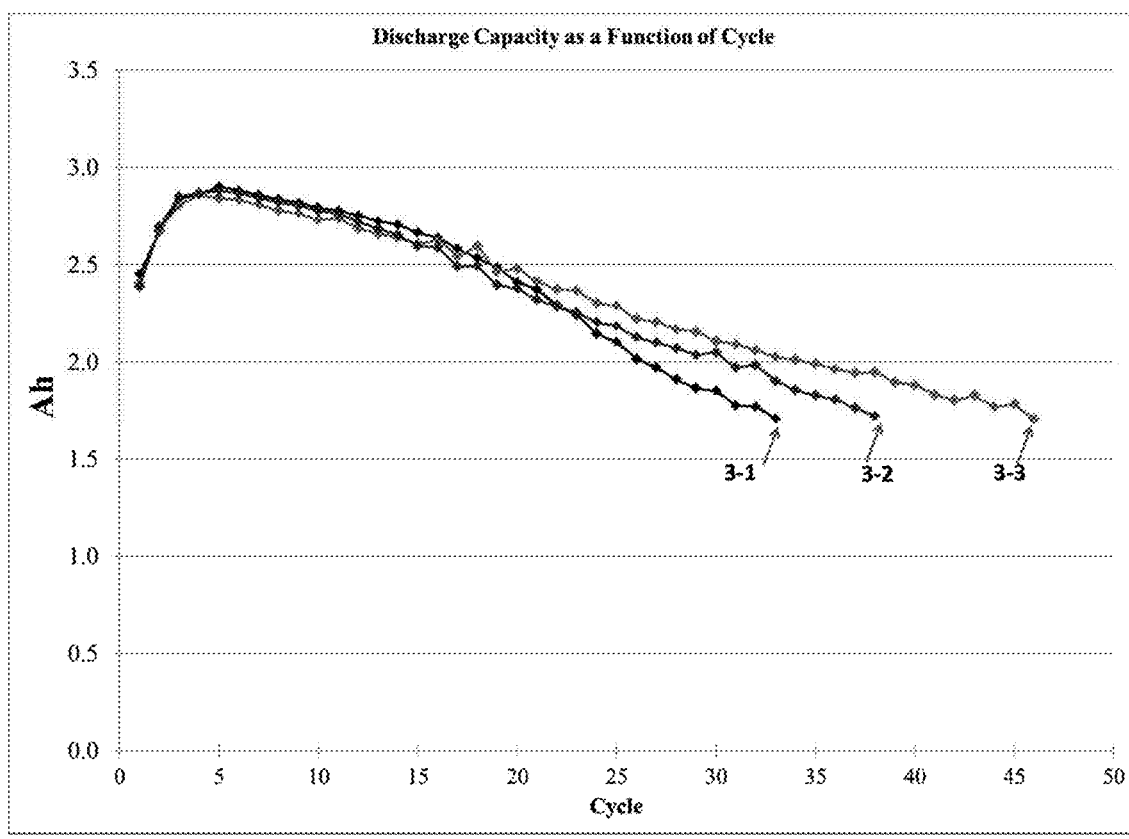

Cycle life delivered by three electrolytes is listed below and shown in FIG. 4:

Electrolyte 3-1: 33 cycles (Comparative Electrolyte)
Electrolyte 3-2: 40 cycles
Electrolyte 3-3: 46 cycles This example shows the life cycle improvement of electrochemical cells including additives described herein for lithium cells having a sulfur cathode.

Example 4

This example illustrates the life cycle improvement of additives combined with $LiNO_3$.

Cells were assembled with Nickel Cobalt Manganese (NCM) cathode received from Enertech (Korea). Vacuum deposited Li anode with thickness of 8 um and a Celgard 2325 separator were used. The cathode total active area was 99.441 cm². Four kinds of cells were assembled:

- Cell 1: NCM cathode, 8 um Li anode and 0.55 ml of Electrolyte 4-1 (Ethylene Carbonate 44.1 wt %, Dimethyl Carbonate 44.1 wt %, $LiPF_6$ 11.8 wt %).
- Cell 2: NCM cathode, 8 um Li anode and 0.55 ml of Electrolyte 4-2 (98 wt % of Electrolyte 4-1 and 2 wt % of Potassium Ethyl Xanthate).
- Cell 3: NCM cathode treated with solution of $LiNO_3$ in methanol and then dried at 130° C. Amount of $LiNO_3$ in the dry cathode was 0.1 mg/cm². Cathode was combined with 8 micron thickness Li anode and 0.55 ml of Electrolyte 4-1.
- Cell 4: Cathode with $LiNO_3$ from 3 was combined with 8 um Li anode and 0.55 ml of Electrolyte 4-2 (98 wt % of Electrolyte 4-1 and 2 wt % of Potassium Ethyl Xanthate).

Figure 5:
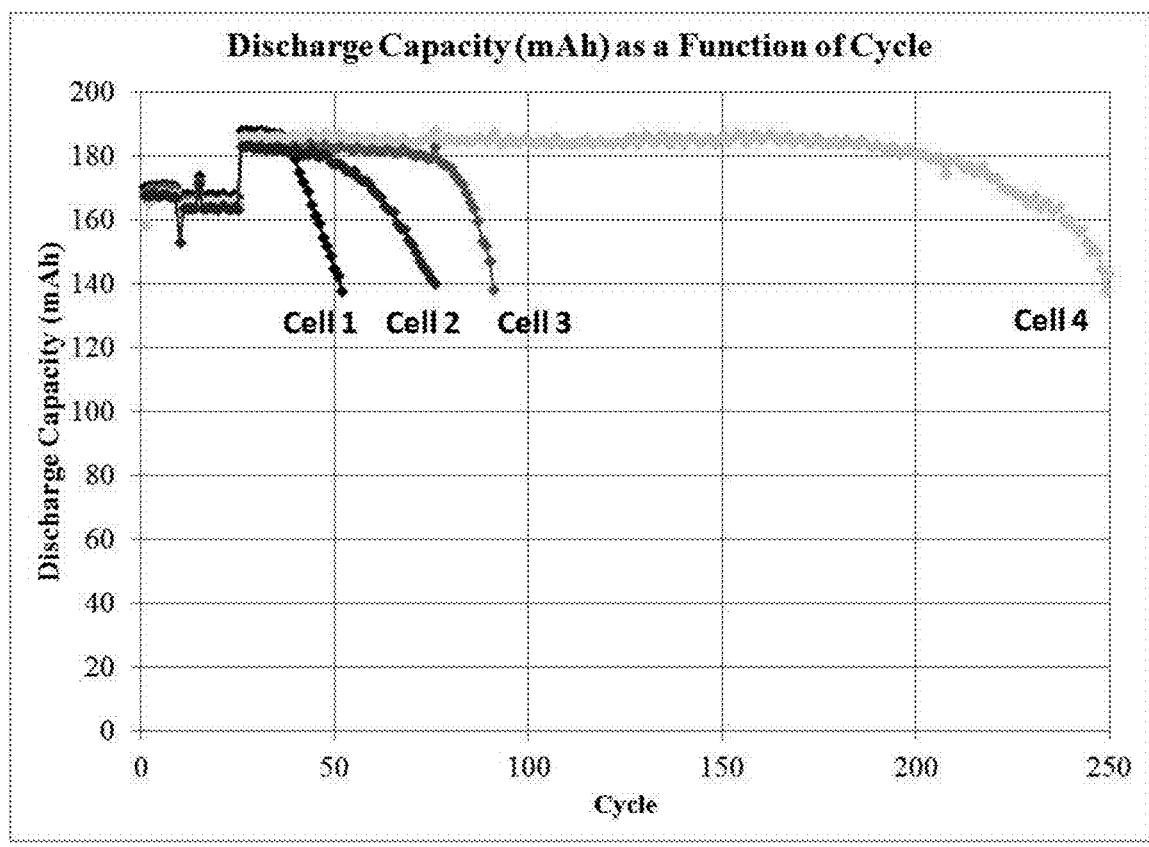

Each cell was sealed in the pouch made of Showa Denko packaging material. Cells electrical testing was performed while applying 10 kg/cm² of anisotropic pressure perpendicular to the surface of the electrodes. Cells at the first 25 cycles were charged at a current of 20 mA to a voltage of 4.20 V and discharged at a current of 34 mA to a voltage of 3.2 V. After 25 cycles charge voltage was increased to 4.35 V. All cells delivered discharge capacity of 183-188 mAh. The cell cycle life was evaluated to the point when discharge capacity dropped below 140 mAh. Cycle life for each cell is listed below and shown in FIG. 5:

- Cell 1: 52 cycles
- Cell 2: 77 cycles
- Cell 3: 91 cycle
- Cell 4: 250 cycles

This example shows the life cycle improvement of electrochemical cells including additives described herein for lithium cells having a nickel cobalt manganese cathode.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding,"

"composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An electrochemical cell, comprising:
a first electrode;
an electrolyte comprising a fluorinated carbonate;
an additive having a structure as in Formula (I) and/or an additive precursor having a structure as in Formula (II):

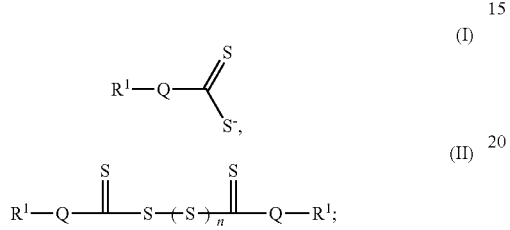

wherein:
each occurrence of Q is independently selected from the group consisting of Se, O, S, $PR^2$, $CR^2_2$, and $SiR^2_2$;
n is 1-6; and
each $R^1$ and $R^2$ are the same or different, optionally connected, and are independently selected from the group consisting of hydrogen; oxygen; sulfur; halogen; nitrogen; phosphorus; substituted or unsubstituted, branched or unbranched aliphatic; substituted or unsubstituted cyclic; substituted or unsubstituted, branched or unbranched acyclic; substituted or unsubstituted, branched or unbranched heteroaliphatic; substituted or unsubstituted, branched or unbranched acyl; substituted or unsubstituted aryl; and substituted or unsubstituted heteroaryl.

2. An electrochemical cell, comprising:
a first electrode;
an electrolyte comprising a fluorinated carbonate;
an additive having a structure as in Formula (I) and/or an additive precursor having a structure as in Formula (II):

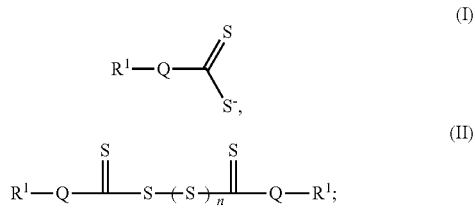

wherein:
each occurrence of Q is independently selected from the group consisting of Se, O, S, $PR^2$, $NR^2$, $CR^2_2$, and $SiR^2_2$;
n is 1-6;
each $R^1$ and $R^2$ are the same or different, optionally connected, and are independently selected from the group consisting of hydrogen; oxygen; sulfur; halogen; nitrogen; phosphorus; substituted or unsubstituted, branched or unbranched aliphatic; substituted or unsubstituted cyclic; substituted or unsubstituted, branched or unbranched acyclic; substituted or unsubstituted, branched or unbranched heteroaliphatic; substituted or unsubstituted, branched or unbranched acyl; substituted or unsubstituted aryl; and substituted or unsubstituted heteroaryl.

3. An electrochemical cell, comprising:
a first electrode comprising a first active electrode species;
an electrolyte comprising a fluorinated carbonate;
an additive having a structure as in Formula (I) and/or an additive precursor having a structure as in Formula (II):

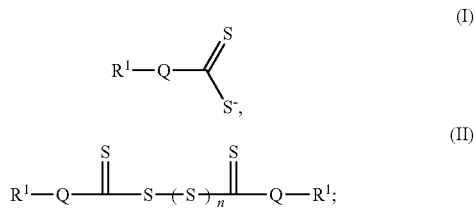

wherein:
each occurrence of Q is independently selected from the group consisting of Se, O, S, $PR^2$, $NR^2$, $CR^2_2$, and $SiR^2_2$;
n is 1-6;
each $R^1$ and $R^2$ are the same or different, optionally connected, and are independently selected from the group consisting of hydrogen; oxygen; sulfur; halogen; nitrogen; phosphorus; substituted or unsubstituted, branched or unbranched aliphatic; substituted or unsubstituted cyclic; substituted or unsubstituted, branched or unbranched acyclic; substituted or unsubstituted, branched or unbranched heteroaliphatic; substituted or unsubstituted, branched or unbranched acyl; substituted or unsubstituted aryl; and substituted or unsubstituted heteroaryl; and
wherein the additive and/or the additive precursor is/are different from the first electrode species.

4. The electrochemical cell of claim 2, wherein the fluorinated carbonate comprises fluorinated ethylene carbonate.

5. The electrochemical cell of claim 2, further comprising a lithium salt.

6. The electrochemical cell of claim 2, wherein the additive and/or additive precursor is polyanionic.

7. The electrochemical cell of claim 2, wherein the additive is a salt.

8. The electrochemical cell of claim 2, wherein the additive comprises a cation.

9. The electrochemical cell of claim 8, wherein the cation is selected from the group consisting of $Li^+$, $Na^+$, $K^+$, $Cs^+$, $Rb^+$, $Ca^{+2}$, $Mg^{+2}$, substituted or unsubstituted ammonium, guanidinium and imidazolium.

10. The electrochemical cell of claim 2, wherein the additive and/or additive precursor comprises a xanthate group.

11. The electrochemical cell of claim 2, wherein at least a portion of the additive and/or additive precursor is in solid form.

12. The electrochemical cell of claim 2, wherein at least a portion of the additive and/or additive precursor is dissolved in the electrolyte.

13. The electrochemical cell of claim 2, wherein the additive and/or additive precursor is disposed on and/or within the first electrode.

14. The electrochemical cell of claim 2, wherein the electrochemical cell comprises a second electrode, and the additive and/or additive precursor is disposed on and/or within the second electrode.

15. The electrochemical cell of claim 2, wherein the electrochemical cell comprises a second electrode, and wherein the second electrode is an intercalated electrode.

16. the electrochemical cell of claim 2, wherein the additive and any additive precursor is present in the electrolyte in a total amount ranging between about 0.5 wt % and about 20 wt % versus the total weight of the electrolyte and additive and/or additive precursor.

17. The electrochemical cell of claim 2, the electrochemical cell comprises a second electrode, and wherein the additive and any additive precursor is present in the electrolyte in a total amount ranging between about 0.5 wt % and about 4 wt % versus the weight of each of the first and second electrodes.

18. The electrochemical cell of claim 2, the electrochemical cell comprises a second electrode, and wherein the additive and/or additive precursor is disposed on and/or within a separator positioned between the first electrode and the second electrode.

19. The electrochemical cell of claim 2, wherein the electrolyte comprises a nitrate.

20. The electrochemical cell of claim 2, further comprising a lithium bis-oxalatoborate species.

* * * * *